United States Patent
Fife et al.

(10) Patent No.: US 9,671,363 B2
(45) Date of Patent: Jun. 6, 2017

(54) CHEMICAL SENSOR WITH CONSISTENT SENSOR SURFACE AREAS

(71) Applicant: LIFE TECHNOLOGIES CORPORATION, Carlsbad, CA (US)

(72) Inventors: Keith G. Fife, Palo Alto, CA (US); Jordan Owens, Austin, TX (US); Shifeng Li, Fremont, CA (US); James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/939,101

(22) Filed: Nov. 12, 2015

(65) Prior Publication Data

US 2016/0077045 A1   Mar. 17, 2016

Related U.S. Application Data

(62) Division of application No. 14/198,417, filed on Mar. 5, 2014, now abandoned.

(60) Provisional application No. 61/900,907, filed on Nov. 6, 2013, provisional application No. 61/790,866, filed on Mar. 15, 2013.

(51) Int. Cl.
  *G01N 27/414* (2006.01)
  *H01L 21/28* (2006.01)
  *B01L 3/00* (2006.01)

(52) U.S. Cl.
  CPC ...... *G01N 27/414* (2013.01); *B01L 3/502761* (2013.01); *G01N 27/4148* (2013.01); *H01L 21/28273* (2013.01); *B01L 2200/0668* (2013.01); *B01L 2300/0636* (2013.01); *B01L 2300/0877* (2013.01); *G01N 27/4145* (2013.01)

(58) Field of Classification Search
  CPC .............. G01N 27/414; G01N 27/4148; H01L 21/28273; B01L 3/502761; B01L 2200/0668; B01L 2300/0636
  USPC ..... 438/49, 66, 201, 211, 257; 257/253, 315
  See application file for complete search history.

(56) References Cited

U.S. PATENT DOCUMENTS

| | | | |
|---|---|---|---|
| 4,086,642 | A | 4/1978 | Yoshida et al. |
| 4,411,741 | A | 10/1983 | Janata |
| 4,437,969 | A | 3/1984 | Covington et al. |
| 4,438,354 | A | 3/1984 | Haque et al. |

(Continued)

FOREIGN PATENT DOCUMENTS

| | | |
|---|---|---|
| CN | 1582334 | 2/2005 |
| CN | 1585896 | 2/2005 |

(Continued)

OTHER PUBLICATIONS

European Search Report for European Application No. EP10780935 mailed Jun. 9, 2015, 5 pages.

(Continued)

*Primary Examiner* — Thinh T Nguyen

(57) ABSTRACT

A chemical sensor is described. The chemical sensor includes a chemically-sensitive field effect transistor including a floating gate conductor having an upper surface. A material defines an opening extending to the upper surface of the floating gate conductor, the material comprising a first dielectric underlying a second dielectric. A conductive element contacts the upper surface of the floating gate conductor and extending a distance along a sidewall of the opening.

8 Claims, 25 Drawing Sheets

(56) References Cited

U.S. PATENT DOCUMENTS

| | | |
|---|---|---|
| 4,444,644 A | 4/1984 | Hiramoto |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,082,788 A | 1/1992 | Farnsworth et al. |
| 5,110,441 A | 5/1992 | Kinlen et al. |
| 5,113,870 A | 5/1992 | Rossenfeld |
| 5,126,022 A | 6/1992 | Soane et al. |
| 5,126,759 A | 6/1992 | Small et al. |
| 5,132,418 A | 7/1992 | Caruthers et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A * | 4/1995 | Baxter ............... H01L 27/0248 438/237 |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A * | 8/1999 | Rosenblatt ......... G01N 27/4148 204/416 |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,091,059 B2 | 8/2006 | Rhodes |
| 7,097,973 B1 | 8/2006 | Zenhausern |
| 7,105,300 B2 | 9/2006 | Parce et al. |
| 7,106,089 B2 | 9/2006 | Nakano et al. |
| 7,173,445 B2 | 2/2007 | Fujii et al. |
| 7,190,026 B2 | 3/2007 | Lotfi et al. |

(56) References Cited

U.S. PATENT DOCUMENTS

| | | | |
|---|---|---|---|
| 7,192,745 | B2 | 3/2007 | Jaeger |
| 7,193,453 | B2 | 3/2007 | Wei et al. |
| 7,211,390 | B2 | 5/2007 | Rothberg |
| 7,223,540 | B2 | 5/2007 | Pourmand et al. |
| 7,226,734 | B2 | 6/2007 | Chee et al. |
| 7,235,389 | B2 | 6/2007 | Lim et al. |
| 7,238,323 | B2 | 7/2007 | Knapp et al. |
| 7,244,559 | B2 | 7/2007 | Rothberg et al. |
| 7,244,567 | B2 | 7/2007 | Chen |
| 7,264,929 | B2 | 9/2007 | Rothberg et al. |
| 7,264,934 | B2 | 9/2007 | Fuller |
| 7,265,929 | B2 | 9/2007 | Umeda et al. |
| 7,267,751 | B2 | 9/2007 | Gelbart et al. |
| 7,276,749 | B2 | 10/2007 | Martin et al. |
| 7,282,370 | B2 | 10/2007 | Bridgham et al. |
| 7,285,384 | B2 | 10/2007 | Fan et al. |
| 7,291,496 | B2 | 11/2007 | Holm-Kennedy |
| 7,297,518 | B2 | 11/2007 | Quake et al. |
| 7,298,475 | B2 | 11/2007 | Gandhi et al. |
| 7,303,875 | B1 | 12/2007 | Bock et al. |
| 7,317,216 | B2 | 1/2008 | Holm-Kennedy |
| 7,317,484 | B2 | 1/2008 | Dosluoglu et al. |
| 7,323,305 | B2 | 1/2008 | Leamon et al. |
| 7,335,762 | B2 | 2/2008 | Rothberg et al. |
| 7,359,058 | B2 | 4/2008 | Kranz et al. |
| 7,361,946 | B2 * | 4/2008 | Johnson ............... G01N 27/129 257/253 |
| 7,363,717 | B2 | 4/2008 | Ekseth et al. |
| 7,381,936 | B2 | 6/2008 | Tan et al. |
| 7,394,263 | B2 | 7/2008 | Pechstein et al. |
| 7,419,636 | B2 | 9/2008 | Aker et al. |
| 7,425,431 | B2 | 9/2008 | Church et al. |
| 7,455,971 | B2 | 11/2008 | Chee et al. |
| 7,462,452 | B2 | 12/2008 | Williams et al. |
| 7,462,512 | B2 | 12/2008 | Levon et al. |
| 7,462,709 | B2 | 12/2008 | Jaeger |
| 7,465,512 | B2 | 12/2008 | Wright et al. |
| 7,466,258 | B1 | 12/2008 | Akopyan et al. |
| 7,470,352 | B2 | 12/2008 | Eversmann et al. |
| 7,482,153 | B2 | 1/2009 | Okada et al. |
| 7,482,677 | B2 | 1/2009 | Lee et al. |
| 7,499,513 | B1 | 3/2009 | Tetzlaff et al. |
| 7,515,124 | B2 | 4/2009 | Yaguma et al. |
| 7,575,865 | B2 | 8/2009 | Leamon et al. |
| 7,576,037 | B2 | 8/2009 | Engelhardt et al. |
| 7,595,883 | B1 | 9/2009 | El Gamal et al. |
| 7,605,650 | B2 | 10/2009 | Forbes |
| 7,608,810 | B2 | 10/2009 | Yamada |
| 7,609,093 | B2 | 10/2009 | Sarig et al. |
| 7,609,303 | B1 | 10/2009 | Lee |
| 7,612,817 | B2 | 11/2009 | Tay |
| 7,614,135 | B2 | 11/2009 | Santini, Jr. et al. |
| 7,622,294 | B2 | 11/2009 | Walt et al. |
| 7,667,501 | B2 | 2/2010 | Surendranath et al. |
| 7,733,401 | B2 | 6/2010 | Takeda |
| 7,785,790 | B1 | 8/2010 | Church et al. |
| 7,821,806 | B2 | 10/2010 | Horiuchi |
| 7,842,377 | B2 | 11/2010 | Lanphere et al. |
| 7,842,457 | B2 | 11/2010 | Berka et al. |
| 7,859,029 | B2 | 12/2010 | Lee et al. |
| 7,859,291 | B2 | 12/2010 | Kim |
| 7,875,440 | B2 | 1/2011 | Williams et al. |
| 7,884,398 | B2 | 2/2011 | Levon et al. |
| 7,885,490 | B2 | 2/2011 | Heideman et al. |
| 7,888,708 | B2 * | 2/2011 | Yazawa ............... G01N 27/414 257/253 |
| 7,923,240 | B2 | 4/2011 | Su |
| 7,932,034 | B2 | 4/2011 | Esfandyarpour et al. |
| 7,948,015 | B2 | 5/2011 | Rothberg et al. |
| 7,955,995 | B2 | 6/2011 | Kakehata et al. |
| 7,960,776 | B2 | 6/2011 | Kim et al. |
| 7,981,362 | B2 | 7/2011 | Glezer et al. |
| 8,012,690 | B2 | 9/2011 | Berka et al. |
| 8,017,938 | B2 | 9/2011 | Gomez et al. |
| 8,035,175 | B2 | 10/2011 | Shim et al. |
| 8,052,863 | B2 | 11/2011 | Suzuki et al. |
| 8,067,731 | B2 | 11/2011 | Matyjaszczyk et al. |
| 8,072,188 | B2 | 12/2011 | Yorinobu et al. |
| 8,124,936 | B1 | 2/2012 | Lagna |
| 8,133,698 | B2 | 3/2012 | Silver |
| 8,138,496 | B2 | 3/2012 | Li et al. |
| 8,199,859 | B2 | 6/2012 | Zerbe et al. |
| 8,217,433 | B1 | 7/2012 | Fife |
| 8,227,877 | B2 * | 7/2012 | Lee .................... G01N 27/4145 257/414 |
| 8,231,831 | B2 | 7/2012 | Hartzell et al. |
| 8,232,813 | B2 | 7/2012 | Burdett et al. |
| 8,247,849 | B2 | 8/2012 | Fife et al. |
| 8,248,356 | B2 | 8/2012 | Chen |
| 8,262,900 | B2 | 9/2012 | Rothberg et al. |
| 8,263,336 | B2 | 9/2012 | Rothberg et al. |
| 8,264,014 | B2 | 9/2012 | Rothberg et al. |
| 8,269,261 | B2 | 9/2012 | Rothberg |
| 8,293,082 | B2 | 10/2012 | Rothberg et al. |
| 8,306,757 | B2 | 11/2012 | Rothberg et al. |
| 8,313,625 | B2 | 11/2012 | Rothberg et al. |
| 8,313,639 | B2 | 11/2012 | Rothberg et al. |
| 8,317,999 | B2 | 11/2012 | Rothberg et al. |
| 8,340,914 | B2 | 12/2012 | Gatewood et al. |
| 8,343,856 | B2 | 1/2013 | Therrien et al. |
| 8,349,167 | B2 | 1/2013 | Rothberg et al. |
| 8,357,547 | B2 * | 1/2013 | Lee .................... G01N 27/4145 257/E31.041 |
| 8,361,713 | B2 | 1/2013 | Bridgham et al. |
| 8,415,716 | B2 | 4/2013 | Rothberg et al. |
| 8,426,898 | B2 | 4/2013 | Rothberg et al. |
| 8,426,899 | B2 | 4/2013 | Rothberg et al. |
| 8,435,395 | B2 | 5/2013 | Rothberg et al. |
| 8,441,044 | B2 | 5/2013 | Rothberg et al. |
| 8,445,194 | B2 | 5/2013 | Drmanac et al. |
| 8,445,945 | B2 | 5/2013 | Rothberg et al. |
| 8,449,824 | B2 | 5/2013 | Sun |
| 8,450,781 | B2 | 5/2013 | Rothberg et al. |
| 8,470,164 | B2 | 6/2013 | Rothberg et al. |
| 8,492,800 | B2 | 7/2013 | Rothberg et al. |
| 8,496,802 | B2 | 7/2013 | Rothberg et al. |
| 8,502,278 | B2 | 8/2013 | Rothberg et al. |
| 8,519,448 | B2 | 8/2013 | Rothberg et al. |
| 8,524,057 | B2 | 9/2013 | Rothberg et al. |
| 8,530,941 | B2 | 9/2013 | Rothberg et al. |
| 8,535,513 | B2 | 9/2013 | Rothberg et al. |
| 8,552,771 | B1 | 10/2013 | Jordan et al. |
| 8,558,288 | B2 | 10/2013 | Rothberg et al. |
| 8,575,664 | B2 | 11/2013 | Rothberg et al. |
| 8,592,154 | B2 | 11/2013 | Rearick |
| 8,653,567 | B2 | 2/2014 | Fife |
| 8,658,017 | B2 | 2/2014 | Rothberg et al. |
| 8,685,230 | B2 | 4/2014 | Rothberg et al. |
| 8,685,298 | B2 | 4/2014 | Rockenschaub et al. |
| 8,728,844 | B1 * | 5/2014 | Liu .................... H01L 29/66477 257/252 |
| 8,731,847 | B2 | 5/2014 | Johnson et al. |
| 8,742,469 | B2 | 6/2014 | Milgrew |
| 8,742,472 | B2 | 6/2014 | Rothberg et al. |
| 8,747,748 | B2 * | 6/2014 | Li ....................... G01N 27/414 257/253 |
| 8,748,947 | B2 | 6/2014 | Milgrew et al. |
| 8,764,969 | B2 | 7/2014 | Rothberg et al. |
| 8,766,327 | B2 | 7/2014 | Milgrew |
| 8,766,328 | B2 | 7/2014 | Rothberg et al. |
| 8,786,331 | B2 | 7/2014 | Jordan et al. |
| 8,796,036 | B2 | 8/2014 | Fife et al. |
| 8,821,798 | B2 | 9/2014 | Bustillo et al. |
| 8,841,217 | B1 | 9/2014 | Fife et al. |
| 8,912,005 | B1 | 12/2014 | Fife et al. |
| 8,945,912 | B2 * | 2/2015 | Bashir ................... B82Y 15/00 422/82.01 |
| 8,962,366 | B2 | 2/2015 | Putnam et al. |
| 8,963,216 | B2 | 2/2015 | Fife et al. |
| 8,983,783 | B2 | 3/2015 | Johnson et al. |
| 9,023,674 | B2 * | 5/2015 | Shen .................... G01N 27/4148 257/253 |
| 9,201,041 | B2 * | 12/2015 | Dalton .................. G01N 27/414 |
| 9,270,264 | B2 | 2/2016 | Jordan et al. |

(56) References Cited

U.S. PATENT DOCUMENTS

| | | |
|---|---|---|
| 9,389,199 B2 * | 7/2016 | Cheng .............. G01N 27/4148 |
| 2002/0012933 A1 | 1/2002 | Rothberg et al. |
| 2002/0012937 A1 | 1/2002 | Tender et al. |
| 2002/0042388 A1 | 4/2002 | Cooper et al. |
| 2002/0081714 A1 | 6/2002 | Jain et al. |
| 2002/0085136 A1 | 7/2002 | Moon et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu et al. |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0152994 A1 | 8/2003 | Woudenberg et al. |
| 2003/0155942 A1 | 8/2003 | Thewes |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2004/0002470 A1 | 1/2004 | Keith et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0093645 A1 | 5/2005 | Watanabe et al. |
| 2005/0106587 A1 | 5/2005 | Klapproth et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0239132 A1 | 10/2005 | Klapprith |
| 2005/0282224 A1 | 12/2005 | Fouillet et al. |
| 2006/0000772 A1 | 1/2006 | Sano et al. |
| 2006/0035400 A1 | 2/2006 | Wu et al. |
| 2006/0057025 A1 | 3/2006 | Eversmann et al. |
| 2006/0057604 A1 | 3/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 * | 9/2006 | Migliorato ....... G01N 33/54373 257/253 |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2006/0289726 A1 | 12/2006 | Paulus et al. |
| 2007/0059741 A1 | 3/2007 | Kamahori et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0096216 A1 | 4/2008 | Quake |
| 2008/0111161 A1 | 5/2008 | Sorge et al. |
| 2008/0121946 A1 | 5/2008 | Youn et al. |
| 2008/0136933 A1 | 6/2008 | Dosluoglu et al. |
| 2008/0185616 A1 | 8/2008 | Johnson et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0026082 A1 | 1/2009 | Rothberg et al. |
| 2009/0048124 A1 | 2/2009 | Leamon et al. |
| 2009/0062132 A1 | 3/2009 | Borner |
| 2009/0075383 A1 | 3/2009 | Buschmann et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127689 A1 | 5/2009 | Ye et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0273386 A1 | 11/2009 | Korobeynikow et al. |
| 2010/0007326 A1 | 1/2010 | Nakazato |
| 2010/0026814 A1 | 2/2010 | Shimoda |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0176463 A1 * | 7/2010 | Koizumi .............. G01N 27/414 257/414 |
| 2010/0244106 A1 | 9/2010 | Parker et al. |
| 2010/0273166 A1 | 10/2010 | Garcia |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0236263 A1 | 9/2011 | Sawada et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |

(56) References Cited

U.S. PATENT DOCUMENTS

| | | | |
|---|---|---|---|
| 2012/0045368 A1* | 2/2012 | Hinz | G01N 27/4148 422/69 |
| 2012/0055811 A1 | 3/2012 | Rothberg et al. | |
| 2012/0055813 A1 | 3/2012 | Rothberg et al. | |
| 2012/0056248 A1 | 3/2012 | Fife | |
| 2012/0067723 A1 | 3/2012 | Rearick et al. | |
| 2012/0129703 A1 | 5/2012 | Rothberg et al. | |
| 2012/0129732 A1 | 5/2012 | Rothberg et al. | |
| 2012/0135870 A1 | 5/2012 | Rothberg et al. | |
| 2012/0143531 A1 | 6/2012 | Davey et al. | |
| 2012/0154018 A1 | 6/2012 | Sugiura | |
| 2012/0161207 A1 | 6/2012 | Homyk et al. | |
| 2012/0173159 A1 | 7/2012 | Davey et al. | |
| 2012/0261274 A1 | 10/2012 | Rearick et al. | |
| 2012/0286771 A1 | 11/2012 | Rothberg et al. | |
| 2012/0326213 A1 | 12/2012 | Bustillo et al. | |
| 2012/0326767 A1 | 12/2012 | Milgrew | |
| 2012/0329043 A1 | 12/2012 | Milgrew | |
| 2012/0329192 A1 | 12/2012 | Bustillo et al. | |
| 2013/0001653 A1 | 1/2013 | Milgrew et al. | |
| 2013/0009214 A1 | 1/2013 | Bustillo et al. | |
| 2013/0105868 A1* | 5/2013 | Kalnitsky | G01N 27/414 257/288 |
| 2013/0210128 A1 | 8/2013 | Rothberg et al. | |
| 2013/0210182 A1 | 8/2013 | Rothberg et al. | |
| 2013/0210641 A1 | 8/2013 | Rothberg et al. | |
| 2013/0217004 A1 | 8/2013 | Rothberg et al. | |
| 2013/0217587 A1 | 8/2013 | Rothberg et al. | |
| 2013/0281307 A1 | 10/2013 | Li et al. | |
| 2013/0324421 A1 | 12/2013 | Rothberg et al. | |
| 2013/0341734 A1* | 12/2013 | Merz | G01N 27/26 257/414 |
| 2014/0080717 A1 | 3/2014 | Li et al. | |
| 2014/0148345 A1 | 5/2014 | Li et al. | |
| 2014/0234981 A1 | 8/2014 | Zarkesh-Ha et al. | |
| 2014/0235452 A1 | 8/2014 | Rothberg et al. | |
| 2014/0235463 A1 | 8/2014 | Rothberg et al. | |
| 2014/0308752 A1* | 10/2014 | Chang | G01N 27/4145 436/501 |
| 2015/0097214 A1* | 4/2015 | Chen | G01N 27/4145 257/253 |
| 2016/0178568 A1* | 6/2016 | Cheng | G01N 27/4148 257/253 |

FOREIGN PATENT DOCUMENTS

| | | |
|---|---|---|
| CN | 1703623 | 11/2005 |
| CN | 1826525 | 8/2006 |
| CN | 101669026 | 3/2010 |
| CN | 101676714 | 3/2010 |
| CN | 102203282 | 9/2011 |
| DE | 4232532 | 4/1994 |
| DE | 4430811 | 9/1995 |
| DE | 19512117 | 10/1996 |
| DE | 102008012899 | 9/2009 |
| EP | 0223618 | 5/1987 |
| EP | 1243925 A2 | 9/2002 |
| EP | 1243925 A3 | 3/2003 |
| EP | 1371974 | 12/2003 |
| EP | 1432818 | 6/2004 |
| EP | 1542009 | 6/2005 |
| EP | 1557884 | 7/2005 |
| EP | 1975246 | 3/2007 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | 2000055874 | 2/2000 |
| JP | 2002-272463 | 9/2002 |
| JP | PCT/JP2003/04697 | 4/2003 |
| JP | 2003-279532 | 10/2003 |
| JP | 2004-510125 | 4/2004 |
| JP | 2005218310 | 8/2004 |
| JP | 2004-271384 | 9/2004 |
| JP | 2005/077210 | 3/2005 |
| JP | 2005-515475 | 5/2005 |
| JP | 2005-207797 | 8/2005 |
| JP | 2006138846 | 6/2006 |
| JP | 2006-284225 | 10/2006 |
| JP | 2007/243003 | 9/2007 |
| JP | 2008-215974 | 9/2008 |
| JP | 2010513869 | 4/2010 |
| JP | 2011-525810 | 9/2011 |
| JP | 2012-506557 | 3/2012 |
| JP | 2015-506557 | 3/2012 |
| KR | 10-0442838 | 7/2004 |
| KR | 10-0455283 | 10/2004 |
| TW | 200946904 | 11/2009 |
| WO | 89/09283 | 10/1989 |
| WO | 98/13523 | 4/1998 |
| WO | 98/46797 | 10/1998 |
| WO | 01/20039 | 3/2001 |
| WO | 01/42498 | 6/2001 |
| WO | 01/47804 | 7/2001 |
| WO | 01/81896 | 11/2001 |
| WO | 02/077287 | 10/2002 |
| WO | 02/086162 | 10/2002 |
| WO | 03/073088 | 9/2003 |
| WO | 2004/017068 | 2/2004 |
| WO | 2004/040291 | 5/2004 |
| WO | 2004/048962 | 6/2004 |
| WO | WO-2004/081234 | 9/2004 |
| WO | 2005/015156 | 2/2005 |
| WO | 2005/022142 | 3/2005 |
| WO | 2005/043160 | 5/2005 |
| WO | 2005/047878 | 5/2005 |
| WO | 2005/054431 | 6/2005 |
| WO | 2005062049 | 7/2005 |
| WO | 2005/073706 | 8/2005 |
| WO | 2005/084367 | 9/2005 |
| WO | 2005/090961 | 9/2005 |
| WO | 2005090961 | 9/2005 |
| WO | 2006/005967 | 1/2006 |
| WO | 2006/022370 | 3/2006 |
| WO | 2006/056226 | 6/2006 |
| WO | 2007002204 | 1/2007 |
| WO | 2007/086935 | 8/2007 |
| WO | 2008/007716 | 1/2008 |
| WO | 2008/058282 | 5/2008 |
| WO | 2008/076406 | 6/2008 |
| WO | 2008076406 | 6/2008 |
| WO | 2008/107014 | 9/2008 |
| WO | 2008/133719 | 11/2008 |
| WO | 2009/012112 | 1/2009 |
| WO | 2009/041917 | 4/2009 |
| WO | 2009074926 | 6/2009 |
| WO | 2009/081890 | 7/2009 |
| WO | 2009/158006 | 12/2009 |
| WO | 2010/008480 | 1/2010 |
| WO | 2010/047804 | 4/2010 |
| WO | 2010/138182 | 12/2010 |
| WO | 2010/138186 | 12/2010 |
| WO | 2010/138188 | 12/2010 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/006222 | 1/2012 |
| WO | 2012/046137 | 4/2012 |
| WO | 2012/152308 | 11/2012 |
| WO | 2014/077783 | 5/2014 |

OTHER PUBLICATIONS

European Search Report for European Application No. EP15170247.9 mailed Nov. 10, 2015, 4 pages.

(56) References Cited

OTHER PUBLICATIONS

International Preliminary Report on Patentability for International Application No. PCT/US2014/040923 mailed Dec. 15, 2015, 8 pages.
Ligler, Frances S. et al., "Array biosensor for detection of toxins", *Anal. Bioanal Chem* vol. 377, 2003, pp. 469-477.
Matula, Richard A., "Electrical Resistivity of Copper, Gold, Palladium, and Silver", *Journal of Physical and Chemical Reference Data*, vol. 8.4, 1979, pp. 1147-1298.
Rowe, Chris A. et al., "An Array Immunosensor for Simultaneous Detection of Clinical Analytes", *Anal. Chem.* vol. 71, 1999, pp. 433-439.
Supplementary European Search Report for European Application No. EP10780935 mailed Sep. 30, 2015, 6 pages.
Izuru, Shinmura, "Kojien", *published by Owanami, Fourth Edition*, 1991, p. 2683.
Nakazato, Kazuo, "An Integrated ISFET Sensor Array", *Sensors*, vol. 9, No. 11, 2009, pp. 8831-8851.
Wen-Yaw, Chung A. et al., "New ISFET interface circuit design with temperature Compensation", *CiteSeerx*—URL: http://citeseerx.ist.psu.edu/viewdoc/download?doi=10.1.1.95.2321&rep=rep1&type=pdf, 2006, 1.
0V5640 Datasheet Product Specification, *1/4" color CMOS QSXGA (5 megapixel) image sensor with OmniBSI technology*, May 1, 2011, p. 1, line 9 and pp. 2-7, paragraph 1.
International Search Report and Written Opinion of the International Searching Authority for International Application No. PCT/US2015/066023 mailed Mar. 14, 2016, 18 pages.
International Search Report and Written Opinion of the International Searching Authority for International Application No. PCT/US2015/066052 mailed Apr. 7, 2016, 19 pages.
Liu, Yan et al., "An ISFET based sensing array with sensor offset compensation and pH sensitivity enhancement", *Proc. of 2010 IEEE Int. Symp. on Circuits and Systems (ISCAS)*, ISBN:978-1-4244-5308-5, Jun. 2, 2010, pp. 2283-2286.
Morgenshtein, Arkadiy et al., "Wheatstone-Bridge readout interface for ISFET/REFET applications", *Sensors and Actuators B: Chemical*, vol. 98, No. 1, Mar. 2004, pp. 18-27.
Nakazato, Kazuro, "An Integrated ISFET Sensor Array", *Sensors*, Nov. 2009, vol. 9, No. 11, ISSN:1424-8220, [online], Internet, URL: http://www.mdpi.com/1424-8220/9/11/8831/pdf, Nov. 2009, pp. 8831-8851.
[No Author Listed], "ISFET Wikipedia article", *Wikipedia*, Last modified Nov. 7, 2006, 2006.
Ahmadian, et al., "Single-nucleotide polymorphism analysis by pyrosequencing", *Anal. Biochem,* vol. 280, 2000, 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767,, "Search Information Statement", Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical*, vol. 118, 2006, 41-46.
Bashford, G. et al., "Automated bead-trapping apparatus and control system for single-molecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, "ISFET, Theory and Practice", *IEEE Sensor Conference*, Toronto, Oct. 2003, 2003, pp. 1-26.
Bergveld,, "Thirty years of ISFETOLOGY What happened in the past 30 years and what may happen in the next 30 years", *Sensors and Actuators B*, vol. 88, 2003, pp. 1-20.
Besselink, et al., "ISFET Affinity Sensor", *Methods in Biotechnology*, vol. 7: Affinity Biosensors: Techniques and Protocols, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bockelmann, U. et al., "Detecting DNA by field effect transistor arrays", *Proceedings of the 2006 IFIP International Conference on Very Large Scale Integration*, 2006, 164-168.
Bousse, L. et al., "A process for the combined fabrication of ion sensors and CMOS circuits", *IEEE Electron Device Letters*, vol. 9(1), 1988, pp. 44-46.
Bousse, L. et al., "Zeta potential measurements of Ta2O5 and SiO2 thin films", *J. Colloid Interface Sci.*, vol. 147(1), 1991, pp. 22-32.
Chan, Wai P. et al., "An Integrated ISFETs Instrumentation System in Standard CMOS Technology", *IEEE Journal of Solid-State Circuits*, vol. 45, No. 9, Sep. 2010, pp. 1923-1934.
Chen, Y. et al., "Nanoscale field effect transistor for biomolecular signal amplification", *App Phys Letter*, vol. 91, 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chin, Yuan-Lung et al., "Titanium Nitride Membrane Application to Extended Gate Field Effect Transistor pH Sensor Using VLSI Technology", *Jpn. J. Appl. Phys.* vol. 40, Part 1, No. 11, Nov. 2001, pp. 6311-6315.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-76.
Chung, et al., "ISFET interface circuit embedded with noise rejection capability", *Electronics Letters*, vol. 40, No. 18, Oct. 2004, 1115-1116.
Chung, W-Y et al., "ISFET performance enhancement by using the improved circuit techniques", *Sensors and Actuators B*, vol. 113, 2006, pp. 555-562.
Chung, W-Y et al., "New ISFET interface circuit design with temperature compensation", *Microelectronics Journal*, vol. 37(10), Oct. 1, 2006, pp. 1105-1114.
Chung, W-Y et al., "Temperature compensation electronics for ISFET readout applications", *Biomedical Circuits and Systems*, IEEE International Workshop Singapore, Dec. 1, 2004, pp. 305-308.
Dazhong, Z. et al., "Research of CMOS Biosensor IC for Extracellular Electrophysiological Signal Recording and pH value Measuring", *Solid-State and Integrated-Circuit Technology, 9th International Conference*, NJ USA, Oct. 20, 2008, pp. 2557-2560.
Dorf, Richard C., "The Electrical Engineering Handbook", *University of California, Davis, CRC Press, 2 edition, Chapter 3—Linear Circuit Analysis*, Jun. 25, 2004, pp. 3-1 to 3-66.
Eijkel, J. et al., "Measuring Donnan-related phenomena using a solid-state ion sensor and a concentration-step method", *J. Membrane Sci.*, vol. 127, 1997, pp. 203-221.
Eijkel, J., "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.

(56) References Cited

OTHER PUBLICATIONS

EP09798251.6, "Extend European Search Report" mailed Aug. 27, 2013, 6 pages.
EP09822323.3, "European Extended Search Report" mailed May 27, 2015, 8 pages.
EP10780930, "European Search Report" mailed Jun. 15, 2015, 3 pages.
EP10857377, "European Search Report" mailed Jun. 26, 2015, 3 pages.
EP11801437.2, "European Extended Search Report" mailed Jul. 25, 2013, 10 pages.
EP11801437.2, "LT00349EP Examination Notification" mailed Feb. 12, 2015, 8 pages.
EP11801439.8, "Extended Search Report" mailed Mar. 7, 2014, 9 pages.
EP11804218.3, "European Extended Search Report" mailed Jul. 11, 2013, 3 pages.
EP11827128.7, "European Search Report" mailed Aug. 1, 2013, 5 pages.
EP13161312.7, "Extend European Search Report" mailed Oct. 15, 2013, 8 pages.
EP13163995.7, "EP Search Report" mailed Jul. 9, 2014.
EP13163995.7, "Extend European Search Report" mailed Aug. 20, 2013, 6 pages.
EP13164768.7, "European Search Report" mailed Aug. 20, 2013, 6 pages.
EP13174555.6, "EP Extended Search Report" mailed Dec. 12, 2013, 8 pages.
EP13174555.6, "EP Search Report" mailed Nov. 21, 2013, 5 pages.
EP13177039.8, "EP Search Report" mailed Nov. 21, 2013, 9 pages.
EP13177590.0, "EP Search Report" mailed Nov. 20, 2013, 5 pages.
EP13177590.0, "European Examination Notification" mailed Sep. 8, 2014, 9 pages.
EP14152861.2, "EP Search Report" mailed Jul. 7, 2014, 5 pages.
EP7867780.4, "Examination Report" mailed Jul. 3, 2012.
Eriksson, J. et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128 × 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . . ", *17.3.2 CHEMFET Sensors*, 1996, pp. 499- 501.
Fritz, J. et al., "Electronic detection of DNA by its intrinsic molecular charge", *PNAS*, vol. 99, No. 22, Oct. 2002, 14142-14146.
Gardner, J.W. et al., "Enhancing electronic nose performance by sensor selection using a new integer-based genetic algorithm approach", *Science Direct, Sensors and Actuators B*, vol. 106, 2005, pp. 114-121.
GB0811656.8, "Search and Examination Report" mailed Mar. 12, 2010.
GB0811656.8, "Search Report" mailed Sep. 21, 2009.
GB0811657.6,"Examination Report" mailed Jun. 30, 2010.
GB0811657.6, "Search Report under Section 17" mailed Oct. 26, 2009.
Gracia, I. et al., "Test Structures for ISFET Chemical Sensors", *Proc IEEE 1992 Intl Conf Microelec Test Struct*, vol. 5, 1992, pp. 156-159.
Hammond, et al., "Performance and system-on-chip integration of an unmodified CMOS ISFET", *Science Direct, Sensors and Actuators* vol. 111-112, 2005, pp. 254-258.

Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6-µm CMOS Process", *IEEE Sensors Journal*, vol. 4(6), 2004, 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hamster ovary cell line using Illumina sequencing technology", *BMC Genomics*, vol. 12:67, 2011, pp. 1-8.
Han, Y , "Label-free detection of biomolecules by a field-effect transistor microarray biosensor with bio-functionalized gate surfaces", Masters Dissertation, 2006, pp. 1-63.
Hanshaw, R. et al., "An indicator displacement system for fluorescent detection of phosphate oxyanions under physiological conditions", *Science Direct, Tetrahedron Letters*, vol. 45, Nov. 15, 2004, pp. 8721-8724.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, et al., "Identification of a Single Nucleotide Polymorphism in the MXA Gene Promoter (T/T at nt -88) Correlated with the Response of Hepatitis C Patients to Interferon", *Intervirology*, vol. 43, 2000, 124-127.
Hizawa, et al., "Sensing Characteristics of Charge Transfer Type pH Sensor by Accumulative Operation", *IEEE Sensors. EXCO*, Daegu, Korea, Oct. 22-25, 2006, pp. 144-147.
Hizawa, T et al., "Fabrication of a two-dimensional pH image sensor using a charge transfer technique", *Sensors and Actuators B Chemical*, vol. 117, 2006, 509-515.
Hizawa, T. et al., "32 × 32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, 2007, pp. 1311-1312.
Ingebrandt, Sven et al., "Label-free detection of DNA using field-effect transistors", *Phys. stat. sol. (a) 203*, No. 14, 2006, pp. 3399-3411.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360 .
Ji, H. et al., "Contact Imaging: Simulation and Experiment", *IEEE Trans Circuits Systems-I:Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M. , "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Krause, M. et al., "Extended gate electrode arrays for extracellular signal recordings", *Sensors and Actuators B*, vol. 70, 2000, pp. 101-107.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.

(56) References Cited

OTHER PUBLICATIONS

Leamon, J. et al., "Cramming More Sequencing Reactions onto Microreactor Chips", *Chemical Reviews*, vol. 107, 2007, pp. 3367-3376

Lee, C-S et al., "Ion-sensitive Field-Effect Transistor for Biological Sensing", *Sensors*, vol. 9, 2009, pp. 7111-7131.

Lee, S. et al., "An Enhanced Glucose Biosensor Using Charge Transfer Techniques", *Biosensors and Bioelectronics*, vol. 24, 2008, pp. 650-656.

Li, et al., "Sequence-Specific Label-Free DNA Sensors Based on Silico Nanowires", *Nano Letters*, vol. 4, No. 2, 2004, 245-247.

Lin, B.J. et al., "Practicing the Novolac deep-UV portable conformable masking technique", *Journal of Vacuum Science and Technology*, Vo. 19, No. 4, 1981, 1313-1319.

Lohrengel, M. et al., "A new microcell or microreactor for material surface investigations at large current densities", *Electrochimica Acta*, vol. 49, 2004, pp. 2863-2870.

Lui, A. et al., "A Test Chip for ISFET/CMNOS Technology Development", *Proc. of the 1996 IEEE Intl. Conf. on Microelectronic Test Structures*, vol. 9, 1996, pp. 123-128.

Maki, W et al., "Nanowire-transistor based ultra-sensitive DNA methylation detection", *Biosensors & Bioelectronics*, 23, 2008, pp. 780-787.

Margulies, et al., "Genome sequencing in microfabricated high-density picolitre reactors", *Nature*, vol. 437 (15), Jul. 31, 2005, 376-380.

Marshall, et al., "DNA chips: an array of possibilities", *Nature Biotechnology*, vol. 16, 1998, 27-31.

Martinoia, S. et al., "A behavioral macromodel of the ISFET in Spice", *Sensors Actuators B*, vol. 62, 2000, pp. 182-189.

Martinoia, S. et al., "Development of ISFET Array-Based Microsystems for Bioelectrochemical measurements of cell populations", *Biosensors & Bioelectronics*, vol. 16, 2001, pp. 1043-1050.

Matsuo, J. et al., "Charge Transfer Type pH Sensor with Super High Sensitivity", *The 14th international conference on solid-state sensors actuators and microsystems*, France, Jun. 10- 14, 2007, pp. 1881-1884.

Medoro, G. et al., "A Lab-on-a-Chip for Cell Detection and Manipulation", *IEEE Sensors J*, vol. 3(3), 2003, pp. 317-325.

Meyburg, et al., "N-Channel field-effect transistors with floating gates for extracellular recordings", *Biosens Bioelectron*, vol. 21(7), 2006, pp. 1037-1044.

Milgrew, et al., "The fabrication of scalable multi-sensor arrays using standard CMOS technology", *2003 IEEE Custom Integrated Circuits Conference*, 2003, pp. 513-516.

Milgrew, M. et al., "A 16 × 16 CMOS proton camera array for direct extracellular imaging of hydrogen-ion activity", *IEEE Intl Solid-State Circuits Conf*, Session 32:24, 2008, pp. 590-591; 638.

Milgrew, M. et al., "A large transistor based sensor array chip for direct extracellular imaging", *Sensors and Actuators B Chemical*, vol. 111-112, 2005, 347-353.

Milgrew, M. et al., "Matching the transconductance characteristics of CMOS ESFET arrays by removing trapped charge", *IEEE Trans Electron Devices*, vol. 55(4), 2008, pp. 1074-1079.

Milgrew, M. et al., "Microsensor Array Technology for Direct Extracellular Imaging", Apr. 5, 2006, pp. 1-23.

Milgrew, M. et al., "The development of scalable sensor arrays using standard CMOS technology", *Sensors and Actuators B*, vol. 103, 2004, 37-42.

Milgrew, M.J. et al., "The development of scalable sensor arrays using standard CMOS technology", *ScienceDirect, Sensors and Actuators*, vol. 103, 2004, pp. 37-42.

Milgrew, Mark J. et al., "A Proton Camera Array Technology for Direct Extracellular Ion Imaging", *IEEE International Symposium on Industrial Electronics*, 2008, 2051-2055.

Miyahara, Y. et al., "Biochip Using Micromachining Technology", *J. Institute of Electrostatics*, Japan, vol. 27, No. 6, 2003, 268-272.

Miyahara, Y. et al., "Direct Transduction of Primer Extension into Electrical Signal Using Genetic Field Effect Transistor", *Micro Total Analysis Systems 2004*, vol. 1, 2004, pp. 303-305.

Miyahara, Y. et al., "Potentiometric Detection of DNA Molecules Using Field Effect Transistor", *The Japan Society of Applied Physics*, No. 3 (Translation included), 2003, 1180, 30A-S2.

Naidu, M. S. et al., "Introduction to Electrical Engineering", Chapter 1—Fundamental Concepts of Electricity, *McGraw Hill Education (India) Private Limited*, 1995, pp. 1-10.

Neaman, Donald A. , "Electronic Circuit Analysis and Design", *McGraw Hill Higher Education, 2nd edition*, Chapter 6—Basic FET Amplifiers, (reference will be uploaded in 2 parts due to size) part 1 of 2, Dec. 1, 2000, pp. 313-345.

Neaman, Donald A. , "Electronic Circuit Analysis and Design", *McGraw Hill Higher Education, 2nd edition*, Chapter 6—Basic FET Amplifiers, (reference will be uploaded in 2 parts due to size) part 2 of 2, Dec. 1, 2000, pp. 346-381.

Nishiguchi, K. et al., "Si nanowire ion-sensitive field-effect transistors with a shared floating gate", *Applied Physics Letters* vol. 94, 2009, pp. 163106-1 to 163106-3.

Nyren, P. et al., "Enzymatic Method for Continuous Monitoring of Inorganic Pyrophosphate Synthesis", *Analytical Biochemistry*, vol. 151, 1985, pp. 504-509.

Oelbner, W. et al., "Encapsulation of ESFET sensor chips", *Sensors Actuators B*, vol. 105, 2005, pp. 104-117.

Oelbner, W. et al., "Investigation of the dynamic response behaviour of ISFET ph sensors by means of laser Doppler velocimetry (LDV)", *Sensor Actuators B*, vol. 26-27, 1995, pp. 345-348.

Offenhausser, A. et al., "Field-Effect transistor array for monitoring electrical activity from mammalian neurons in culture", *Biosensors & Bioelectronics*, vol. 12(8), 1997, pp. 819-826.

Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.

Palan, B. et al., "New ISFET sensor interface circuit for biomedical applications", *Sensors and Actuators B: Chemical: International Journal Devoted to Research and Development of Physical and Chemical Transducers*, Elsevier S.A. Ch., vol. 57, No. 1-3, 1999, pp. 63-68.

Park, K-Y et al., "ISFET glucose sensor system with fast recovery characteristics by employing electrolysis", *Sensors and Actuators B: Chemical*, vol. 83 (1-3), Mar. 15, 2002, pp. 90-97.

Patolsky, F. et al., "Nanowire-Based Biosensors", *Analyt Chem 1*, vol. 78(13), 2006, pp. 4261-4269.

PCT/JP2005/001987, "International Search Report" mailed Apr. 5, 2005.

PCT/JP2005/015522, "International Preliminary Report on Patentability" mailed Mar. 19, 2007.

PCT/JP2005/015522, "International Search Report" (includes English translation) mailed Sep. 27, 2005.

PCT/US/2009/05745, "International Preliminary Report on Patentability" mailed Apr. 26, 2011.

PCT/US/2009/05745, "International Search Report and Written Opinion" mailed Dec. 11, 2009.

PCT/US2007/025721, "Declaration of Non-Establishment of International Search Report" mailed Jul. 15, 2008.

PCT/US2007/025721, "International Preliminary Report on Patentability" mailed Jun. 16, 2009.

PCT/US2007/025721, "Written Opinion" mailed Jun. 16, 2009.

PCT/US2009/003766, "International Preliminary Report on Patentability" mailed Jan. 5, 2011.

PCT/US2009/003766, "International Search Report and Written Opinion" mailed Apr. 8, 2010.

PCT/US2009/003797, "International Search Report and Written Opinion" mailed Mar. 12, 2010.

PCT/US2010/001543, "International Preliminary Report on Patentability" mailed Nov. 29, 2011, pp. 1-8.

PCT/US2010/001543, "International Search Report and Written Opinion" mailed Oct. 13, 2010, pp. 1-12.

PCT/US2010/001553, "International Preliminary Report on Patentability" mailed Dec. 8, 2011, pp. 1-10.

PCT/US2010/001553, "International Search Report and Written Opinion" mailed Jul. 28, 2010, pp. 1-2.

PCT/US2010/048835, "International Preliminary Report on Patentability" mailed Mar. 19, 2013, 7 pages.

(56) References Cited

OTHER PUBLICATIONS

PCT/US2010/48835, "International Search Report and Written Opinion" mailed Dec. 16, 2010, pp. 1-12.
PCT/US2011/042655, "International Search Report" mailed Oct. 21, 2011, pp. 1-2.
PCT/US2011/042660, "International Search Report" mailed Nov. 2, 2011.
PCT/US2011/042665, "International Search Report" mailed Nov. 2, 2011.
PCT/US2011/042668, "International Preliminary Report on Patentability" mailed Mar. 26, 2013, 11 pages.
PCT/US2011/042668, "International Search Report" mailed Oct. 28, 2011.
PCT/US2011/042669, "International Search Report and Written Opinion" mailed Jan. 9, 2012, pp. 1-5.
PCT/US2011/042683, "International Preliminary Report on Patentability" mailed Jun. 4, 2013, 5 pages.
PCT/US2011/042683, "International Search Report and Written Opinion" mailed Feb. 16, 2012.
PCT/US2012/058996, "International Search Report and Written Opinion" mailed Jan. 22, 2013, pp. 1-11.
PCT/US2012/071471, "International Preliminary Report on Patentability" mailed Jun. 24, 2014, 8 pages.
PCT/US2012/071471, "International Search Report of the International Searching Authority and Written Opinion" mailed Apr. 24, 2013, 14 pages.
PCT/US2012/071482, "International Preliminary Amendment" mailed Jun. 24, 2014, 7 pages.
PCT/US2012/071482, "International Search Report of the International Searching Authority and Written Opinion" mailed May 23, 2013, 11 pages.
PCT/US2013/022129, "International Preliminary Report on Patentability" mailed Jul. 22, 2014, 11 pages.
PCT/US2013/022129, "International Search Report of the International Searching Authority and Written Opinion" mailed Aug. 9, 2013, 18 pages.
PCT/US2013/022140, "International Preliminary Report on Patentability" mailed Jul. 22, 2014, 9 pages.
PCT/US2013/022140, "International Search Report of the International Searching Authority and Written Opinion" mailed May 2, 2013, 15 pages.
PCT/US2014/020887, "International Preliminary Report on Patentability" mailed Sep. 15, 2015, 8 pages.
PCT/US2014/020887, "International Search Report and Written Opinion" mailed May 30, 2014, 12 pages.
PCT/US2014/020892, "International Search Report and Written Opinion" mailed Jun. 3, 2014.
PCT/US2014/040923, "International Search Report and Written Opinion" mailed Sep. 1, 2014, 14 pages.
Poghossian, A. et al., "Functional testing and characterization of ISFETs on wafer level by means of a micro-droplet cell", *Sensors*, vol. 6, 2006, pp. 397-404.
Pollack, J. et al., "Genome-wide analysis of DNA copy-numbe changes using cDNA microarrays", Nature Genetics, *Nature America Inc.*, vol. 23, Sep. 1999, pp. 41-46.
Pourmand, N. et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, et al., "Ultra-low power precision ISFET readout using global current feedback", *Electronic Letters*, vol. 42, No. 22, Oct. 2006, 1264-1265.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Drift Reduction in Ion-Sensitive FETs using correlated double sampling", *Electronics Letters*, vol. 43, No. 16, Aug. 2, 2007, 857 (2 pages).
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rodriguez-Villegas, E. , "Solution to trapped charge FGMOS transistors", *Electronics Letters*, vol. 39(19), 2003.
Ronaghi, M. et al., "A Sequencing Method Based on Real-Time Pyrophosphate", *Science*, vol. 281, 1998, 363-365.
Rothberg, J. et al., "An integrated semiconductor device enabling non-optical genome sequencing", *Nature*, vol. 475, No. 7356, Jul. 21, 2011, pp. 348-352.
Sakata, et al., "Potentiometric Detection of DNA Using Genetic Transistor", *Denki Gakkai Kenkyukai Shiryo Chemical Sensor Kenkyukai*, CHS-03-51-55, 2003, 1-5.
Sakata, T. et al., "Cell-based field effect devices fo cell adhesion analysis", *Intl. Conf. on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA cojugate", *Proc. of 2006 Intl. Conf. on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.
Sakata, T. et al., "Direct transduction of allele-specific primer extension into electrical signal using genetic field effect transistor", *Biosensors and Bioelectronics*, vol. 22, 2007, pp. 1311-1316.
Sakata, T. et al., "DNA Analysis Chip Based on Field-Effect Transistors", *Japanese Journal of Applied Physics*, vol. 44(4B), 2005, pp. 2854-2859.
Sakata, T. et al., "DNA Sequencing Based on Intrinsic Molecular Charges", *Angewandte Chemie International Edition 2006*, vol. 118, 2006, 2283-2286.
Sakata, T. et al., "DNA Sequencing Based on Intrinsic Molecular Charges", *Angewandte Chemie International Edition 2006*, vol. 45, 2006, pp. 2225-2228.
Sakata, T. et al., "DNA Sequencing Using Genetic Field Effect Transistor", *13th Intl. Conf. on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator",

(56) References Cited

OTHER PUBLICATIONS

*Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of Single Nucleotide Polymorphism by Using a Genetic Field-effect transistor", *ChemBioChem*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, pp. 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, R. et al., "A new approach to immunoFET operation", *Biosensors & Bioelectronics*, vol. 5, 1990, pp. 103-124.
Schasfoort, R. et al., "Field-effect flow control for microfabricated fluidic networks", *Science*, vol. 286(5441), 1999, pp. 942-945.
Schoning, M. et al., "Bio FEDs (Field-Effect Devices): State-of-the-Art and New Directions", *Electroanalysis*, vol. 18(19-20), 2006, pp. 1893-1900.
Seong-Jin, K. et al., "Label-Free CMOS DNA Quantification With On-Chip Noise Reduction Schemes", *Solid-State Sensors, Actuators and Microsystems Conference, IEEE*, Jun. 10, 2013, pp. 947-950.
SG200903992-6, , "Search and Examination Report (Favourable) Mailed Jan. 20, 2011", 12.
Shah, N., "Microfabrication of a parellel-array DNA pyrosequencing chip", *NNIN REU Research Accomplishments*, 2005, pp. 130-131.
Shepherd, L. et al., "A biochemical translinear principle with weak inversion ISFETs", *IEEE Trans Circuits Syst—I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S15-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, 5354-5361.
Simonian, A. L. et al., "FET based biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Starodub, N. et al., "Immunosensor for the determination of the herbicide simazine based on an ion-selective field-effect transistor", *Analytica Chimica Acta*, vol. 424, 2000, pp. 37-43.
Takenaka, et al., "DNA Sensing on a DNA Probe-Modified Electrode Using Ferrocenylnaphthalene Dimide as the Electrochemically Active Ligand", *Anal. Chem.*, vol. 72, No. 6, 2000, 1334-1341.
Temes, G.C. et al., "A Tutorial Discussion of the Oversampling Method for A/D and D/A Conversion", *1990 IEEE International Symposium on Circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Tokuda, T. et al., "A CMOS image sensor with optical and potential dual imaging function for on-chip bioscientific applications", *Sensors and Actuators A*, vol. 125, No. 2, 2006, 273-280.
Tomaszewski, D. et al., "Electrical characterization of ISFETs", *J Telecomm Info Technol*, Mar. 2007, pp. 55-60.
Toumazou, C. et al., "Using transistors to linearase biochemistry", *Electronics Letters*, vol.43(2), Jan. 18, 2007, 3 pages.
Truman, P., "Monitoring liquid transport and chemical composition in lab on . . . ", *Lab on a Chip*, vol. 6, 2006, pp. 1220-1228
Uslu, F. et al., "Labelfree fully electronic nucleic acid detection system based on a field-effect transistor device", *Biosens & Bioelectron*, vol. 19(12), 2004, pp. 1723-1731.
Van Der Schoot, Bart et al., "The Use of a Multi-ISFET Sensor Fabricated in a Single Substrate", *Letter to the Editors, Sensors and Actuators*, vol. 12, 1987, pp. 463-468.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, "The Development of an ISFET based heparin sensor using the ion-step measuring method", *Biosensors and Bioelectronics*, vol. 9, Nos. 9-10, 1993, 463-472.
Van Kerkhof, , "The Development of an ISFET-based Heparin Sensor", *Thesis*, 1994.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical*, vol. 18-19, 1994, pp. 56-59.
Vardalas, John , "Twists and Turns in the Development of the Transistor", *IEEE—USA Today's Engineer Online*, May 2003, 6 pages.
Voigt, H. et al., "Diamond-like carbon-gate pH-ISFET", *Sensors and Actuators B.*, vol. 44, 1997, pp. 441-445.
Wagner, T et al., "'All-in-one' solid-state device based on a light-addressable potentiometric sensor platform", *Sensors and Actuators B*, vol. 117, 2006, pp. 472-479.
Wang, W. et al., "Label-free detection of small-molecule-protein interactions by using nanowire nanosensors", *Proc. of the Natl. Acad. of Sciences (PNAS)*, vol. 102(9), 2005, pp. 3208-3212.
Wilhelm, D. et al., "pH Sensor Based on Differential Measurements on One pH-FET Chip", *Sensors and Actuators B*, vol. 4, 1991, pp. 145-149.
Woias, P, "Modelling the short time response of ISFET sensors", *Sensors and Actuators B*, vol. 24-25, 1995, pp. 211-217.
Woias, P. et al., "Slow pH response effects of silicon nitride ISFET sensors", *Sensors and Actuators B*, vol. 48, 1998, pp. 501-504.
Wood, et al., "Base composition-independent hybridization in tetramethylammonium chloride: a method for oligonucleotide screening of highly complex gene libraries", *Proceedings of the National Academy of Sciences*, vol. 82, 1985, 1585-1588.
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, vol. 10, 2005, pp. 420-430.
Yeow, T.C.W. et al., "A very large integrated pH-ISFET sensor array chip compatible with standard CMOS processes", *Sensor and Actuators B*, vol. 44, 1997, 434-440.
Yoshida, Shoji et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society* vol. 151(3), 2004, pp. H53-H58.
Yuqing, M. et al., "Ion sensitive field effect trnasducer-based biosensors", *Biotechnology Advances*, vol. 21, 2003, pp. 527-534.
Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.
Zhao, B. et al., "Floating-Gate Ion Sensitive Field-Effect Transistor for Chemical and Biological Sensing", *MRS Proceedings*, vol. 828, 2005, pp. 349-354.

(56) References Cited

OTHER PUBLICATIONS

Zhou, et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, 1-11.

Schroder, Dieter K., "6. Oxide and Interface Trapped Charges, Oxide Thickness", *Semiconductor Material and Device Characterization*, John Wiley & Sons, ISBN: 978-0-471-73906-7, Feb. 17, 2006, pp. 319-387.

\* cited by examiner

CHEMICAL SENSOR WITH CONSISTENT SENSOR SURFACE AREAS

CROSS-REFERENCE TO RELATED APPLICATIONS

This application is a divisional of U.S. patent application Ser. No. 14/198,417 filed Mar. 5, 2014, which claims priority to U.S. Provisional Application No. 61/900,907 filed Nov. 6, 2013 and 61/790,866 filed Mar. 15, 2013, the entire contents of which are incorporated by reference herein in their entirety.

FIELD OF THE INVENTION

The present disclosure relates to sensors for chemical analysis, and to methods for manufacturing such sensors.

BACKGROUND

A variety of types of chemical sensors have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution. Arrays of ISFETs may be used for monitoring chemical reactions, such as DNA sequencing reactions, based on the detection of ions present, generated, or used during the reactions. See, for example, Rothberg et al., U.S. patent application Ser. No. 12/002,291 (now U.S. Pat. No. 7,948,015), filed Dec. 14, 2009, based on U.S. Prov. Pat. Appl. Nos. 60/956,324, filed Aug. 16, 2007, 60/968,748, filed Jul. 10, 2007, and 60/870,073, filed Dec. 14, 2006, which is incorporated by reference herein in its entirety. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

An issue that arises in the operation of large scale chemical sensor arrays is the susceptibility of the sensor output signals to noise. Specifically, the noise affects the accuracy of the downstream signal processing used to determine the characteristics of the chemical and/or biological process being detected by the sensors. In addition, chemical sensor performance variation across the array results in undesirable differences in the sensor output signals, which further complicates the downstream signal processing. It is therefore desirable to provide devices including low noise chemical sensors, and methods for manufacturing such devices.

SUMMARY

In one embodiment, a chemical sensor is described. The chemical sensor includes a chemically-sensitive field effect transistor including a floating gate conductor having an upper surface; a material defining an opening extending to the upper surface of the floating gate conductor, the material comprising a first dielectric underlying a second dielectric; and a conductive element contacting the upper surface of the floating gate conductor and extending a distance along a sidewall of the opening. In an exemplary embodiment, the opening of the chemical sensor may include a lower portion within the first dielectric, and an upper portion within the second dielectric. In another embodiment, a width of the lower portion of the opening is substantially the same as a width of the upper portion. In yet another embodiment, the conductive element is conformal with a shape of the opening. In one embodiment, the conductive element extends to an upper surface of the second dielectric. In an exemplary embodiment, the conductive element includes an inner surface defining a lower portion of a reaction region for the chemical sensor, and the second dielectric includes an inner surface defining an upper portion of the opening. In an exemplary embodiment, the conductive element comprises an electrically conductive material, and an inner surface of the conductive element includes an oxide of the electrically conductive material. In another embodiment, a sensing surface of the chemical sensor includes an inner surface of the conductive element. In yet another embodiment, the chemically-sensitive field effect transistor generates a sensor signal in response to a chemical reaction occurring proximate to the conductive element. In one embodiment, the floating gate conductor comprises a plurality of conductors electrically coupled to one another and separated by dielectric layers, and the floating gate conductor is an uppermost conductor in the plurality of conductors.

In another embodiment, a method for manufacturing a chemical sensor is described. The method includes forming a chemically-sensitive field effect transistor including a floating gate conductor having an upper surface; forming a material defining an opening extending to the upper surface of the floating gate conductor, the material comprising a first dielectric underlying a second dielectric; and forming a conductive element contacting the upper surface of the floating gate conductor and extending a distance along a sidewall of the opening. In an exemplary embodiment, forming the material and forming the conductive element may include forming the first dielectric on the floating gate conductor, the first dielectric defining a cavity extending to the upper surface of the floating gate conductor; forming the second dielectric thereon; etching the second dielectric to expose the conductive element, thereby defining an opening; and forming the conductive element within the opening. According to another embodiment, forming the conductive element within the opening may include depositing a conductive material within the opening and on an upper surface of the first dielectric; and removing at least a portion of the conductive material from the upper surface of the second dielectric. In yet another embodiment, removing at least the portion of the conductive material may comprises depositing a layer of photoresist within the opening; and removing at least a portion of the conductive material together with the photoresist from the upper surface of the second dielectric. In one embodiment, the conductive material comprises titanium. In an exemplary embodiment, the opening is a nanowell. In an exemplary embodiment, the forming a conductive element includes depositing a conductive material conformally within the opening. In another embodiment, the conductive element includes an inner surface defining a lower portion of a reaction region for the chemical sensor, and the second dielectric includes an inner surface defining an upper portion of the opening.

Particular aspects of one embodiment of the subject matter described in this specification are set forth in the drawings and the description below. Other features, aspects, and advantages of the subject matter will become apparent from the description, the drawings, and the claims.

DETAILED DESCRIPTION

Figure 1:
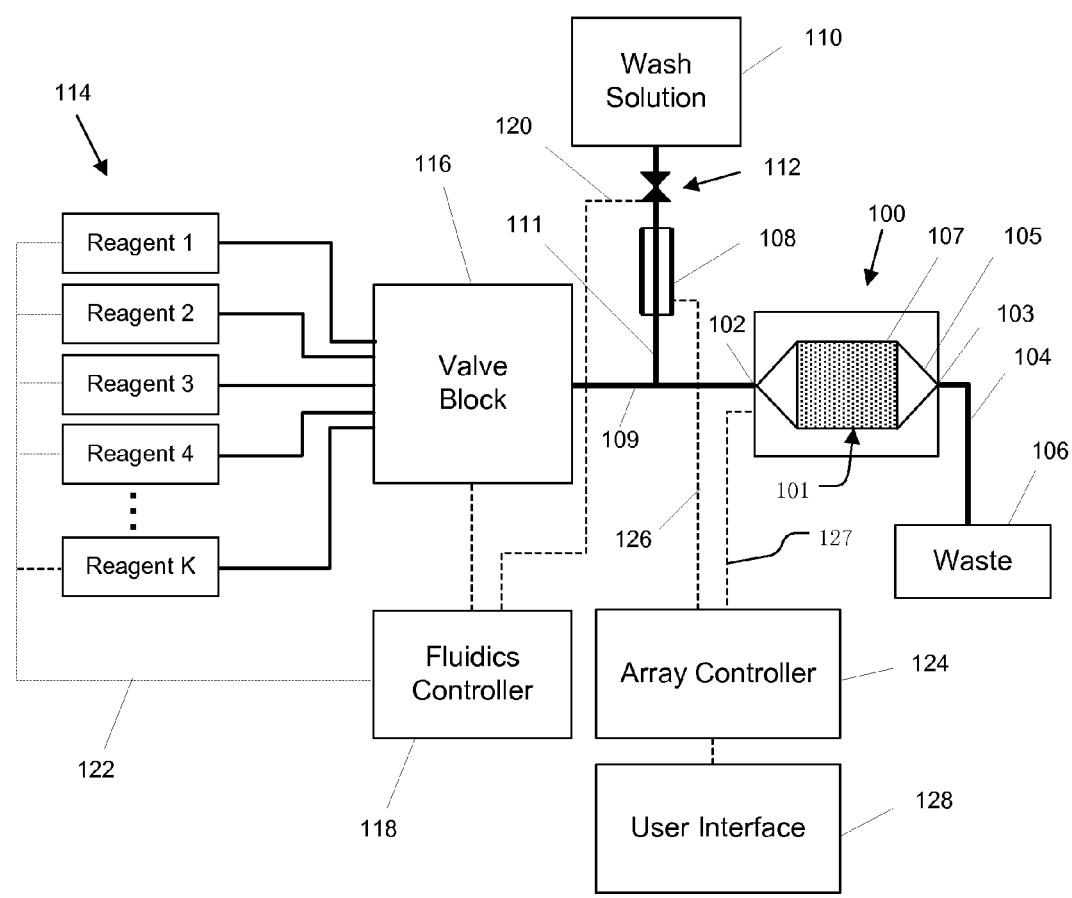
FIG. 1 illustrates a block diagram of components of a system for nucleic acid sequencing according to an exemplary embodiment.

A chemical detection device is described that includes low noise chemical sensors, such as chemically-sensitive field effect transistors (chemFETs), for detecting chemical reactions within overlying, operationally associated reaction regions. Reducing the plan or top view area (or footprint) of individual chemical sensors and the overlying reaction regions allows for higher density devices. However, as the dimensions of the chemical sensors are reduced, Applicants have found that a corresponding reduction in the sensing surface area of the sensors can significantly impact performance. For example, for chemical sensors having sensing surfaces defined at the bottom of the reaction regions, reducing the plan view dimensions (e.g. the width or diameter) of the reaction regions results in a similar reduction in the sensing surface areas. Applicants have found that as the sensing surface area is reduced to technology limits, fluidic noise due to the random fluctuation of charge on the sensing surface contributes to an increasing proportion of the total variation in sensing surface potential. This can significantly reduce the signal-to-noise ratio (SNR) of the sensor output signal, which affects the accuracy of the downstream signal processing used to determine the characteristics of the chemical and/or biological process being detected by the sensor.

Chemical sensors described herein have sensing surface areas which are not limited to a two-dimensional area at the bottom of the reaction regions. In embodiments described herein, the sensing surface of the chemical sensor includes a generally horizontal portion along the bottom surface of the reaction region, as well as a generally vertical portion extending along a sidewall of an opening containing the reaction region. The distance that the generally vertical portion extends along the sidewall is defined by the thickness of a dielectric material that forms a lower portion of the opening. The dielectric material can be deposited using a process (e.g. thin film deposition) which results in very small thickness variation across the array. In doing so, the sensor surface areas of the chemical sensors can be very well controlled, resulting in uniform chemical sensor performance across the array and thus simplifying the downstream signal processing. By extending the sensing surface in the generally vertical direction, the chemical sensor can have a small footprint, while also having a sufficiently large sensing surface area to avoid the noise issues associated with small sensing surfaces. The footprint of a chemical sensor is determined in part by the width (e.g. diameter) of the overlying reaction region and can be made small, allowing for a high density array. In addition, because the sensing surface extends a controlled distance up the sidewall, the sensing surface area can be relatively large. As a result, low noise chemical sensors can be provided in a high density array, such that the characteristics of reactions can be accurately detected.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors as described herein. The flow cell 101 includes an inlet 102, an outlet 103, and a flow chamber 105 defining a flow path for the reagents 114 over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, vacuum, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes reaction regions, also referred to herein as microwells, which are operationally associated with corresponding chemical sensors in the sensor array. For example, each reaction region may be coupled to a chemical sensor suitable for detecting an analyte or reaction property of interest within that reaction region. The microwell array 107 may be integrated in the integrated circuit device 100, so that the microwell array 107 and the sensor array are part of a single device or chip. The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array. The array controller 124 also provides a reference bias voltage to the reference electrode 108 to bias the reagents 114 flowing over the microwell array 107.

During an experiment, the array controller 124 collects and processes output signals from the chemical sensors of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 1. In the illustrated embodiment, the array controller 124 is external to the integrated circuit device 100. In some alternative embodiments, some or all of the functions performed by the array controller 124 are carried out by a controller or other data processor on the integrated circuit device 100. The values of the output signals from the chemical sensors indicate physical and/or chemical parameters of one or more reactions taking place in the corresponding reaction regions in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, each of which are incorporated by reference herein. The user interface 128 may display information about the flow cell 101 and the output signals received from chemical sensors in the sensor array on the integrated circuit device 100. The user interface 128 may also display instrument settings and controls, and allow a user to enter or set instrument settings and controls.

The fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors indicating chemical reactions occurring in response to the delivery of the reagents 114. During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 (and possibly diffusing into passage 111) reach the reference electrode 108. In an exemplary embodiment, the wash solution 110 may be selected as being in continuous contact with the reference electrode 108, which may be especially useful for multi-step reactions using frequent wash steps.

Figure 2:
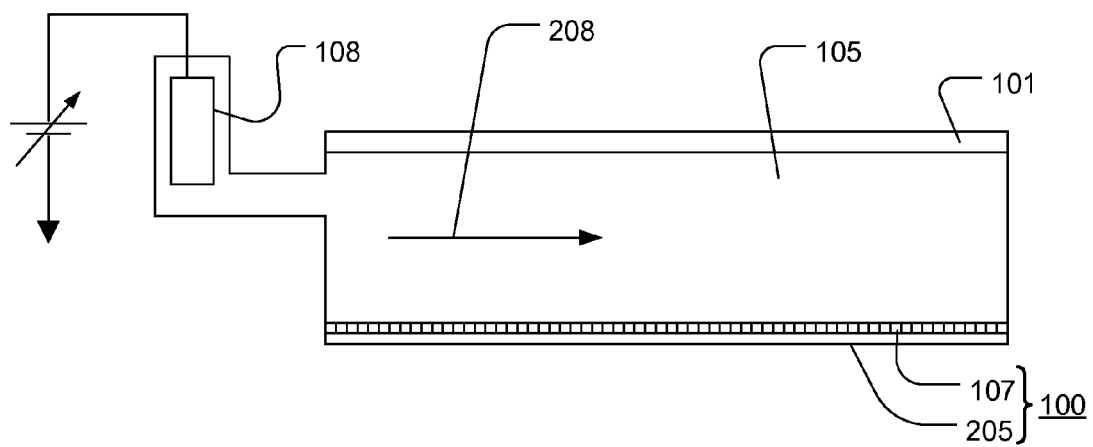
FIG. 2 illustrates a cross-sectional view of a portion of the integrated circuit device and flow cell according to an exemplary embodiment.

FIG. 2 illustrates cross-sectional and expanded views of a portion of the integrated circuit device 100 and flow cell 101. The integrated circuit device 100 includes the microwell array 107 of reaction regions operationally associated with sensor array 205. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed. The chemical sensors of the sensor array 205 are responsive to (and generate output signals related to) chemical reactions within associated reaction regions in the microwell array 107 to detect an analyte or reaction property of interest. The chemical sensors of the sensor array 205 may for example be chemically sensitive field-effect transistors (chemFETs), such as ion-sensitive field effect transistors (ISFETs). Examples of chemical sensors and array configurations that may be used in embodiments are described in Schultz et al., U.S. patent application Ser. No. 12/785,667 (now U.S. Pat. No. 8,546,128), filed May 24, 2010, titled "Fluidics System for Sequential Delivery of Reagents"; Rotherberg et al., U.S. patent application Ser. No. 12/721,458 (now U.S. Pat. No. 8,306,757), filed Mar. 10, 2010, titled "Methods and Apparatus for Measuring Analytes Using Large Scale FET Arrays"; Rotherberg et al., U.S. patent application Ser. No. 12/475,311, filed May 29, 2009, titled "Methods and Apparatus for Measuring Analytes"; Rotherberg et al., U.S. patent application Ser. No. 12/474,897, filed May 29, 2009, titled "Methods and Apparatus for Measuring Analytes"; Rotherberg et al., U.S. patent application Ser. No. 12/002,781, filed Dec. 17, 2007, titled "Methods and Apparatus for Measuring Analytes Using Large Scale FET Arrays"; and U.S. patent application Ser. No. 12/474,897 (now U.S. Pat. No. 7,575,865) filed Aug. 1, 2005, titled "Methods of Amplifying and Sequencing Nucleic Acids", each of which are incorporated by reference herein in their entirety.

Figure 3:
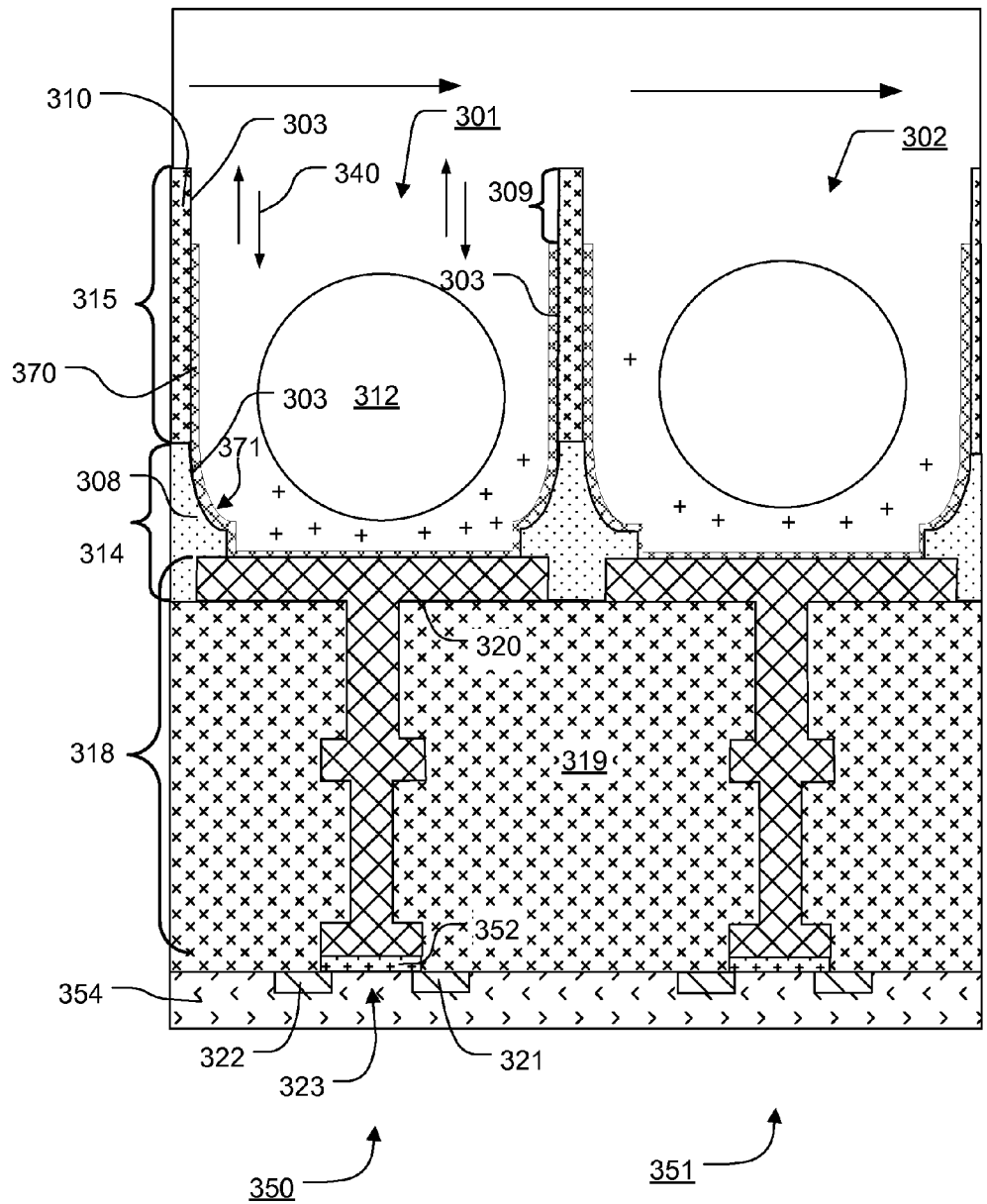
FIG. 3 illustrates a cross-sectional view of two representative chemical sensors and their corresponding reaction regions according to a first embodiment.

FIG. 3 illustrates a cross-sectional view of two representative chemical sensors and their corresponding reaction regions according to a first embodiment. In FIG. 3, two chemical sensors 350, 351 are shown, representing a small portion of a sensor array that can include millions of chemical sensors. Chemical sensor 350 is coupled to corresponding reaction region 301, and chemical sensor 351 is coupled to corresponding reaction region 302. Chemical sensor 350 is representative of the chemical sensors in the sensor array. In the illustrated example, the chemical sensor 350 is a chemically-sensitive field effect transistor (chemFET), more specifically an ion-sensitive field effect transistor (ISFET) in this example. The chemical sensor 350 includes a floating gate structure 318 having a sensor plate 320 coupled to the reaction region 301 by an electrically conductive element 370. As can be seen in FIG. 3, the sensor plate 320 is the uppermost floating gate conductor in the floating gate structure 318. In the illustrated example, the floating gate structure 318 includes multiple patterned layers of conductive material within layers of dielectric material 319.

The chemical sensor 350 also includes a source region 321 and a drain region 322 within a semiconductor substrate 354. The source region 321 and the drain region 322 comprise doped semiconductor material have a conductivity type different from the conductivity type of the substrate 354. For example, the source region 321 and the drain region 322 may comprise doped P-type semiconductor material, and the substrate may comprise doped N-type semiconductor material. Channel region 323 separates the source region 321 and the drain region 322. The floating gate structure 318 overlies the channel region 323, and is separated from the substrate 354 by a gate dielectric 352. The gate dielectric 352 may be for example silicon dioxide. Alternatively, other dielectrics may be used for the gate dielectric 352.

As shown in FIG. 3, the reaction region 301 is within an opening having a sidewall 303 extending through dielectric materials 310, 308 to the upper surface of the sensor plate 320. Each of the dielectric materials 310, 308 may comprise one or more layers of material, such as silicon dioxide or silicon nitride. The opening includes a lower portion 314 within dielectric material 308 and proximate to the sensor plate 320. The opening also includes an upper portion 315 within the dielectric material 310 and extending from the lower portion 314 to the upper surface of the dielectric material 310. In the illustrated embodiment, the width of the upper portion 315 of the opening is substantially the same as the width of the lower portion 314 of the opening. However, depending on the material(s) and/or etch process used to create the opening, the width of the upper portion 315 of the opening may be greater than the width of the lower portion 314 of the opening, or vice versa. The opening may for example have a circular cross-section. Alternatively, the opening may be non-circular. For example, the cross-section may be square, rectangular, hexagonal, or irregularly shaped. The dimensions of the openings, and their pitch, can vary from embodiment to embodiment. In some embodiments, the openings can have a characteristic diameter, defined as the square root of 4 times the plan view cross-sectional area (A) divided by Pi (e.g., sqrt($4*A/\pi$)), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or even not greater than 0.1 micrometers.

The lower portion 314 of the opening includes the electrically conductive element 370 on the sidewall 303 of the dielectric material 310. In the illustrated embodiment, the inner surface 371 of the electrically conductive element 370 defines a lower segment of the reaction region 301. That is, there is no intervening deposited material layer between the inner surface 371 of the electrically conductive element 370 and the reaction region 301 for the chemical sensor 350. As a result of this structure, the inner surface 371 of the electrically conductive element 370 is conformal to the opening and acts as the sensing surface for the chemical sensor 350. It should be understood by those skilled in the art that precise shape and dimension of the electrically conductive element 370, as with all other materials illustrated in the figures, is process dependant.

In the illustrated embodiment, the electrically conductive element 370 is a conformal layer of material within the lower portion 314 of the opening, such that the electrically conductive element 370 extends across the upper surface of the sensor plate 320. In the illustrated embodiment, the electrically conductive element 370 extends beyond the lower portion 314 of the opening and into the upper portion 315 of the opening. The inner surface of the dielectric material 310 defines an upper segment of the reaction region 301. The conductive element 370 may for example extend along at least 5% of the sidewall 303, at least 10%, at least 25%, at least 50%, at least 75%, or at least 85% of the sidewall 303, or even extend along 99% of the sidewall 303. The conformal inner surface 371 of the electrically conductive element 370 allows the chemical sensor 350 to have a small plan view area, while also having a sufficiently large surface area to avoid the noise issues associated with small sensing surfaces. The plan view area of the chemical sensor 350 is determined in part by the width (or diameter) of the reaction region 301 and can be made small, allowing for a high density array. In addition, because the sensing surface extends up the sidewall 303, the sensing surface area depends upon the distance of this extension and the circumference of the reaction region 301, and can be relatively large. As a result, low noise chemical sensors 350, 351 can be provided in a high density array, such that the characteristics of reactions can be accurately detected.

During manufacturing and/or operation of the device, a thin oxide of the material of the electrically conductive element 370 may be grown which acts as a sensing material (e.g. an ion-sensitive sensing material) for the chemical sensor 350. Whether an oxide is formed depends on the conductive material, the manufacturing processes performed, and the conditions under which the device is operated. For example, in one embodiment the electrically conductive element 370 may be titanium nitride, and titanium oxide or titanium oxynitride may be grown on the inner surface 371 of the conductive element 370 during manufacturing and/or during exposure to solutions during use. In the illustrated example, the electrically conductive element 370 is shown as a single layer of material. More generally, the electrically conductive element 370 may comprise one or more layers of a variety of electrically conductive materials, such as metals or ceramics, depending upon the embodiment. The conductive material can be for example a metallic material or alloy thereof, or can be a ceramic material, or a combination thereof. An exemplary metallic material includes one of aluminum, copper, nickel, titanium, silver, gold, platinum, hafnium, lanthanum, tantalum, tungsten, iridium, zirconium, palladium, or a combination thereof. An exemplary ceramic material includes one of titanium nitride, titanium aluminum nitride, titanium oxynitride, tantalum nitride or a combination thereof. In some alternative embodiments, an additional conformal sensing material (not shown) is deposited on the conductive element 370 and within the openings. The sensing material may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the embodiment.

In operation, reactants, wash solutions, and other reagents may move in and out of the reaction region 301 by a diffusion mechanism 340. The chemical sensor 350 is responsive to (and generates an output signal related to) the amount of charge 324 proximate to the conductive element 370. The presence of charge 324 in an analyte solution alters the surface potential at the interface between the conductive element 370 and the analyte solution within the reaction region 301. Changes in the charge 324 cause changes in the voltage on the floating gate structure 318, which in turn changes in the threshold voltage of the transistor. This change in threshold voltage can be measured by measuring the current in the channel region 323 between the source region 321 and a drain region 322. As a result, the chemical sensor 350 can be used directly to provide a current-based output signal on an array line connected to the source region 321 or drain region 322, or indirectly with additional circuitry to provide a voltage-based output signal. Because the charge 324 may be more highly concentrated near the bottom of the reaction region 301, the distance that the conductive element 370 extends up the sidewall 303 of the opening is a tradeoff between the amplitude of the desired signal detected in response to the charge 324, and the fluidic noise due to random fluctuation of charge between the conductive element 370 and the analyte solution. Increasing the distance that the conductive element 370 extends up the sidewall 303 increases the fluidic interface area for the chemical sensor 350, which acts to reduce the fluidic noise. However, due to the diffusion of charge 324 out of the reaction region 301, the concentration of charge 324 decreases with distance from the bottom of the reaction region 301. As a result, upper sidewall segments of the conductive element 370 detect portions of the signal from areas having lower charge concentration, which can reduce the overall amplitude of the desired signal detected by the sensor 350. In contrast, decreasing the distance the conductive element 370 extends up the sidewall 303 reduces the sensing surface area and thus increases the fluidic noise, but also increases the overall amplitude of the desired signal detected by the sensor 350.

For a very small sensing surface area, Applicants have found that the fluidic noise changes as a function of the sensing surface area differently than the amplitude of the desired signal. Because the SNR of the sensor output signal is the ratio of these two quantities, there is an optimal distance the conductive element 370 extends along the sidewall 303 at which SNR is maximum. The optimal distance can vary from embodiment to embodiment depending on the material characteristics of the conductive element 370 and the dielectric material 310, the volume, shape, aspect ratio (such as base width-to-well depth ratio), and other dimensional characteristics of the reaction regions, the nature of the reaction taking place, as well as the reagents, byproducts, or labeling techniques (if any) that are employed. The optimal distance may for example be determined empirically.

As described in more detail below with respect to FIGS. 4 to 12, the distance the conductive element 370 extends along the sidewall 303 is defined by the etch time of the deposited layer, for example. The dielectric material 310 and electrically conductive element 370 can be etched using a timed etch process, for example, which results in selectivity of distance 309 (e.g. the distance dielectric material 310 extends beyond electrically conductive element 370). In doing so, the sensor surface areas of the chemical sensors can be controlled, resulting in uniform chemical sensor performance across the array and simplifying the downstream signal processing.

In an embodiment, reactions carried out in the reaction region 301 can be analytical reactions to identify or determine characteristics or properties of an analyte of interest. Such reactions can generate directly or indirectly byproducts that affect the amount of charge adjacent to the electrically conductive element 370. If such byproducts are produced in small amounts or rapidly decay or react with other constituents, multiple copies of the same analyte may be analyzed in the reaction region 301 at the same time in order to increase the output signal generated. In an embodiment, multiple copies of an analyte may be attached to a solid phase support 312, as shown in FIG. 3, either before or after deposition into the reaction region 301. The solid phase support 312 may be microparticles, nanoparticles, beads, solid or porous gels, or the like. For simplicity and ease of explanation, solid phase support 312 is also referred herein as a particle. For a nucleic acid analyte, multiple, connected copies may be made by rolling circle amplification (RCA), exponential RCA, Recombinase Polymerase Amplification (RPA), Polymerase Chain Reaction amplification (PCR), emulsion PCR amplification, or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

Figure 4:
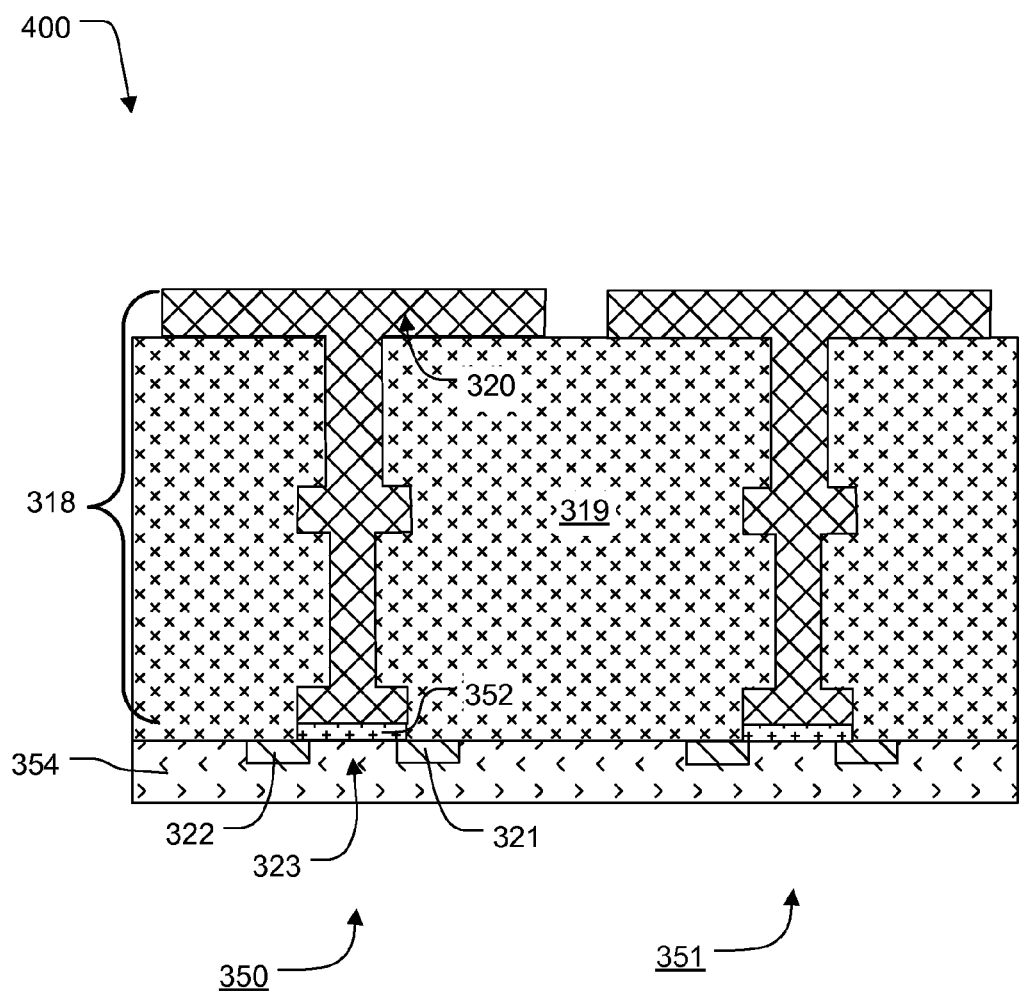
FIGS. 4 to 12 illustrate stages in a manufacturing process for forming an array of chemical sensors and corresponding reaction regions according to a first embodiment.

FIGS. 4 to 12 illustrate stages in a manufacturing process for forming an array of chemical sensors and corresponding reaction regions according to a first embodiment. FIG. 4 illustrates a structure 400 formed in a first stage. The structure 400 includes the floating gate structures (e.g. floating gate structure 318) for the chemical sensors 350, 351. The structure 400 can be formed by depositing a layer of gate dielectric material on the semiconductor substrate 354, and depositing a layer of polysilicon (or other electrically conductive material) on the layer of gate dielectric material. The layer of polysilicon and the layer gate dielectric material can then be etched using an etch mask to form the gate dielectric elements (e.g. gate dielectric 352) and the lowermost conductive material element of the floating gate structures. Following formation of an ion-implantation mask, ion implantation can then be performed to form the source and drain regions (e.g. source region 321 and a drain region 322) of the chemical sensors. A first layer of the dielectric material 319 can then be deposited over the lowermost conductive material elements. Conductive plugs can then be formed within vias etched in the first layer of dielectric material 319 to contact the lowermost conductive material elements of the floating gate structures. A layer of conductive material can then be deposited on the first layer of the dielectric material 319 and patterned to form second conductive material elements electrically connected to the conductive plugs. This process can then be repeated multiple times to form the completed floating gate structure 318 shown in FIG. 4. Alternatively, other and/or additional techniques may be performed to form the structure. Forming the structure 400 in FIG. 4 can also include forming additional elements such as array lines (e.g. row lines, column lines, etc.) for accessing the chemical sensors, additional doped regions in the substrate 354, and other circuitry (e.g. select switches, access circuitry, bias circuitry etc.) used to operate the chemical sensors, depending upon the device and array configuration in which the chemical sensors described herein are implemented. In some embodiments, the elements of the structure may for example be manufactured using techniques described in Schultz et al., U.S. patent application Ser. No. 12/785,667 (now U.S. Pat. No. 8,546,128), filed May 24, 2010, titled "Fluidics System for Sequential Delivery of Reagents"; Rotherberg et al., U.S. patent application Ser. No. 12/721,458 (now U.S. Pat. No. 8,306,757), filed Mar. 10, 2010, titled "Methods and Apparatus for Measuring Analytes Using Large Scale FET Arrays"; Rotherberg et al., U.S. patent application Ser. No. 12/475,311, filed May 29, 2009, titled "Methods and Apparatus for Measuring Analytes"; Rotherberg et al., U.S. patent application Ser. No. 12/474,897, filed May 29, 2009, titled "Methods and Apparatus for Measuring Analytes"; Rotherberg et al., U.S. patent application Ser. No. 12/002,781, filed Dec. 17, 2007, titled "Methods and Apparatus for Measuring Analytes Using Large Scale FET Arrays"; and U.S. patent application Ser. No. 12/474,897 (now U.S. Pat. No. 7,575,865) filed Aug. 1, 2005, titled "Methods of Amplifying and Sequencing Nucleic Acids", which were incorporated by reference in their entirety above.

Figure 5:
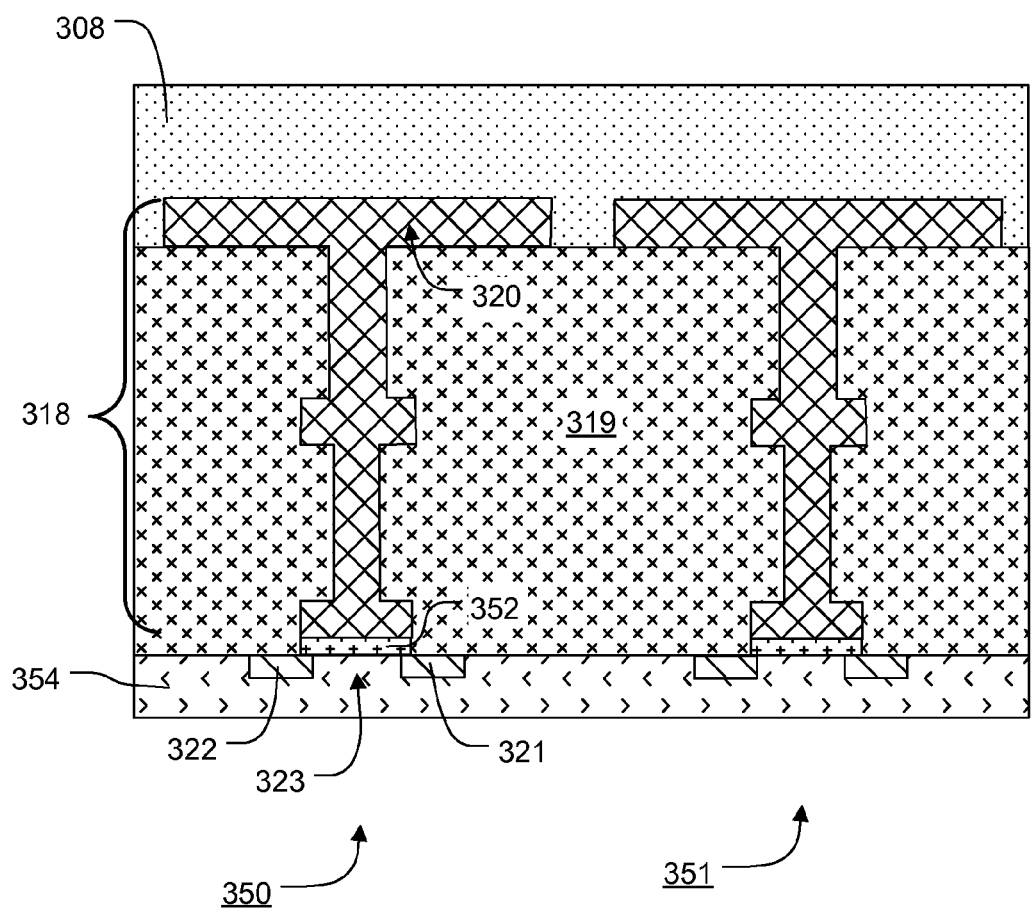
Figure 6:
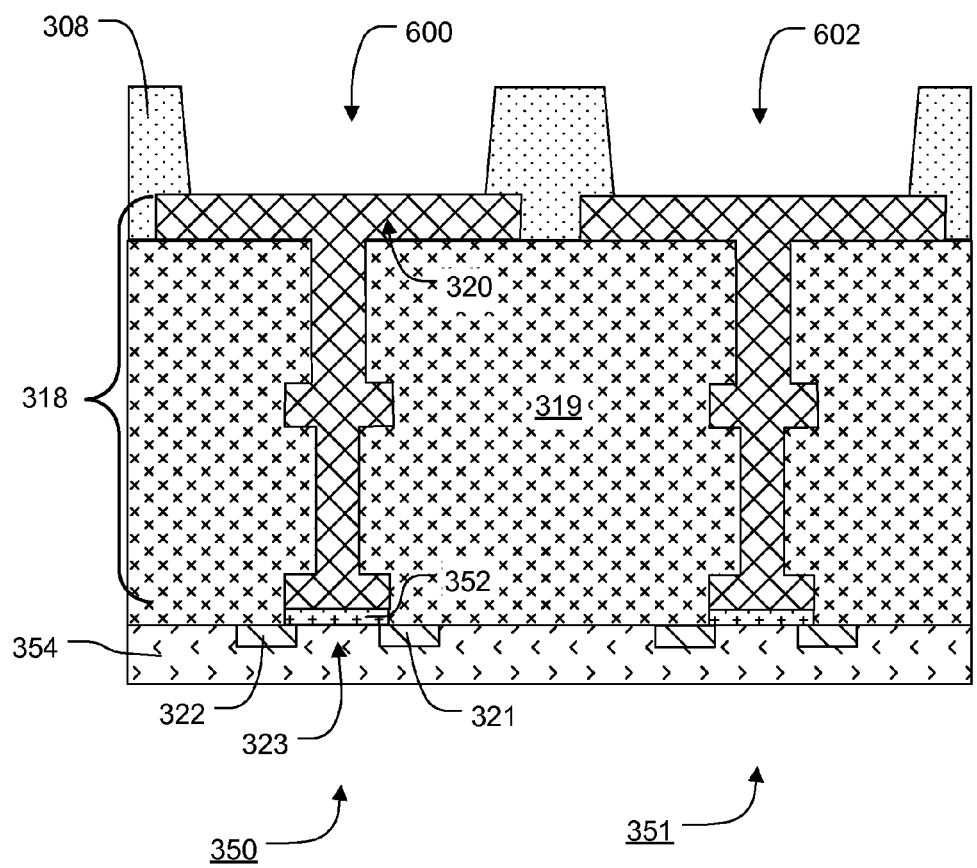
Figure 7:
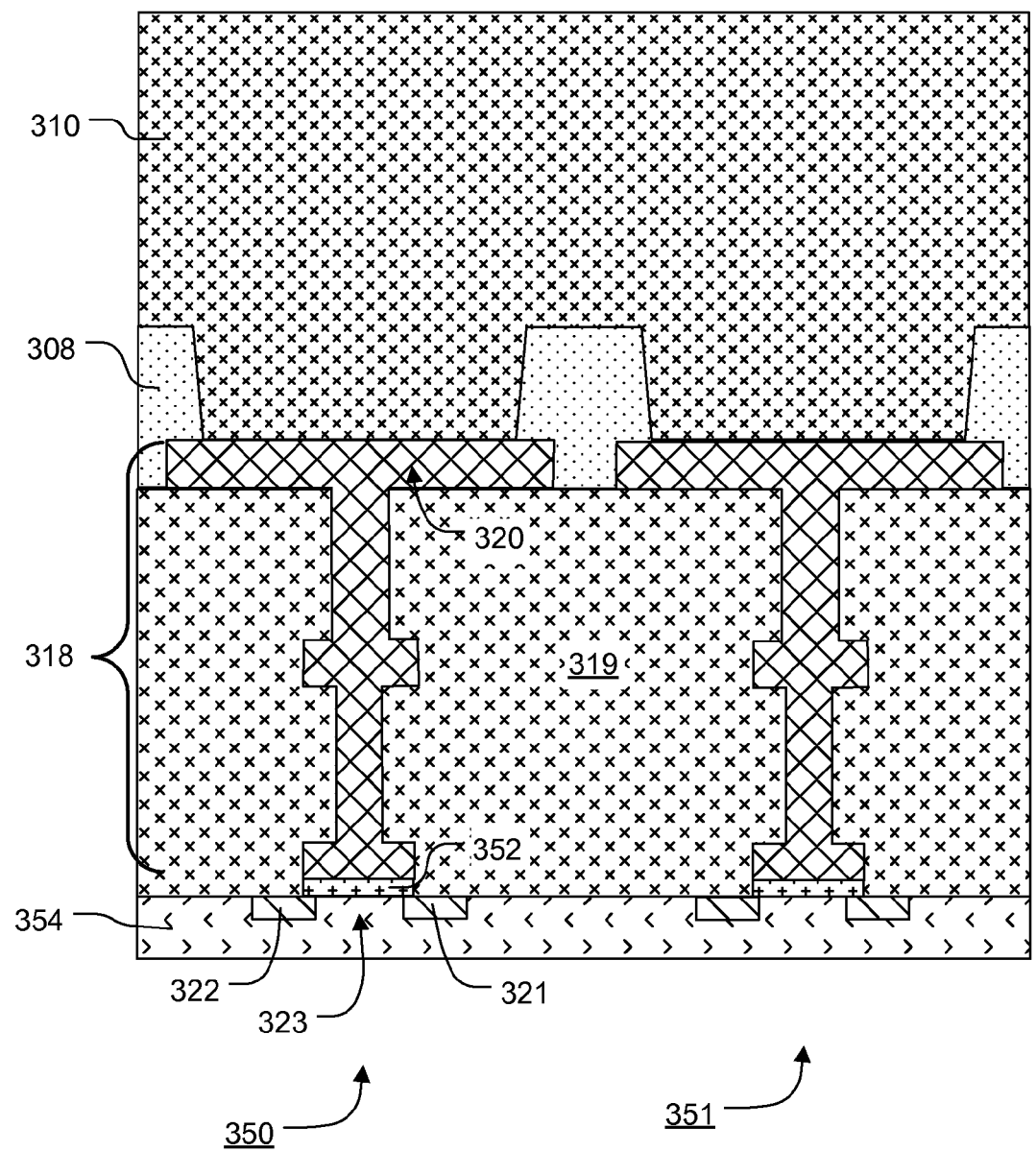

Next, dielectric material 308 having a given thickness is deposited on the structure 400 illustrated in FIG. 4, resulting in the structure illustrated in FIG. 5. The dielectric material 308 comprises one or more dielectric layers of dielectric. The dielectric material 308 may be deposited using a process which results in very small variation in the thickness across the array. For example, the dielectric material 308 may comprise silicon oxide and be deposited using high density plasma (HDP) deposition. Various other techniques may be used, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc. Next, the dielectric material 308 of the structure in FIG. 5 is etched to form cavities 600, 602 extending to the upper surfaces of the floating gate structures of the chemical sensors 350, 351, resulting in the structure illustrated in FIG. 6. The cavities 600, 602 may for example be formed by using a lithographic process to pattern a layer of photoresist on the dielectric material 308 to define the locations of the cavities 600, 602, and then anisotropically etching the dielectric material 308 using the patterned photoresist as an etch mask. The anisotropic etching of the dielectric material 308 may for example be a dry etch process, such as a fluorine based Reactive Ion Etching (RIE) process. Next, dielectric material 310 is formed on the structure illustrated in FIG. 6, resulting in the structure illustrated in FIG. 7. The dielectric material 310 may comprise one or more layers of deposited dielectric material, such as silicon dioxide or silicon nitride.

Figure 8:
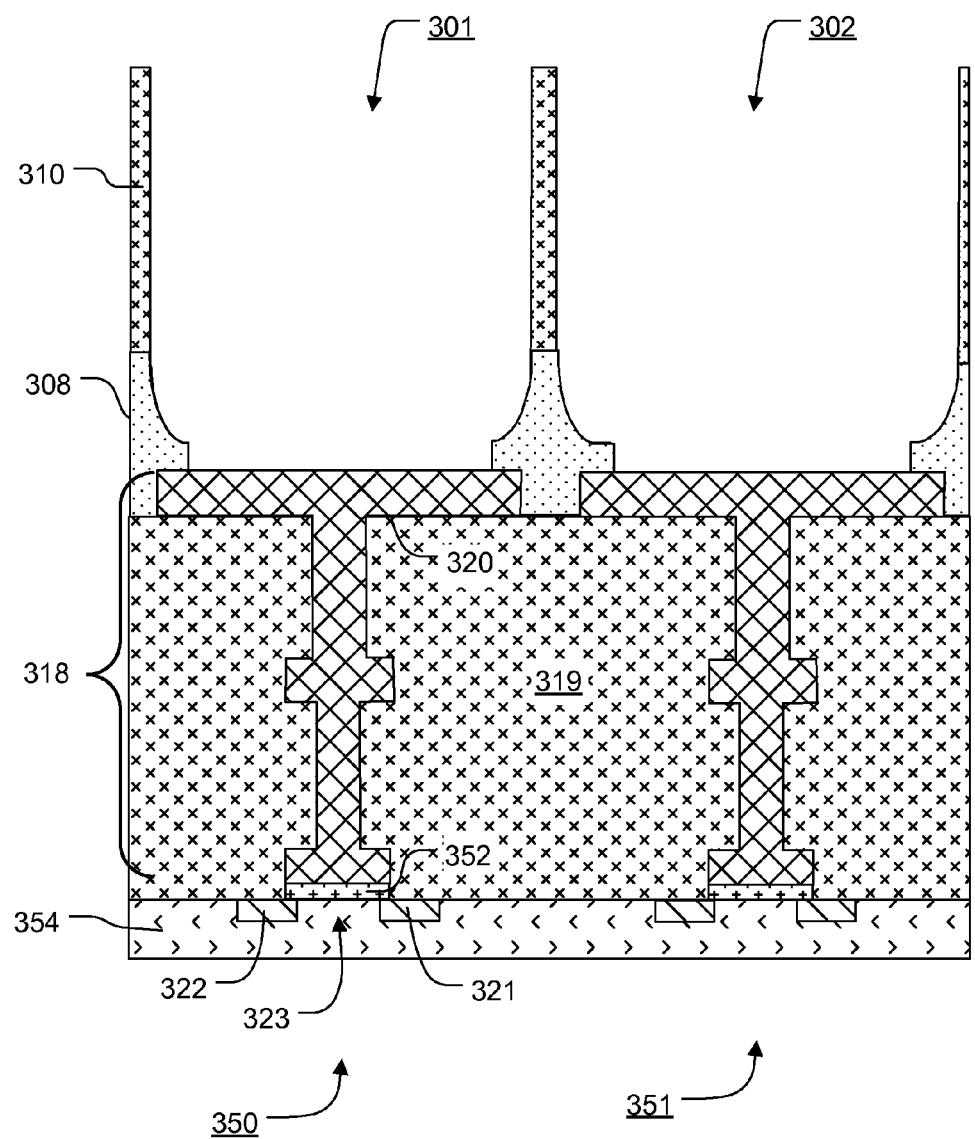

Next, dielectric material 310 is etched to form openings defining reaction regions 301, 302 extending to the sensor plate 320, resulting in the structure illustrated in FIG. 8. Next, a conformal layer of conductive material 900 is deposited on the structure illustrated in FIG. 8, resulting in the structure illustrated in FIG. 9. The conductive material 900 comprises one or more layers of electrically conductive material. For example, the conductive material 900 may be a layer of titanium nitride, or a layer of titanium. Alternatively, other and/or additional conductive materials may be used, such as those described above with reference to the conductive element 370. In addition, more than one layer of conductive material may be deposited. The conductive material 900 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc. In contemplated embodiments, conductive element 370 may be formed to take various shapes and thicknesses that may be determined based on material and techniques described above. For example, instead of the depiction of conductive element 370 as illustrated in FIG. 3, one may imagine conductive element 370 is formed such that it is conformal with the solid support (rounded to follow the shape of solid support 312).

Figure 9:
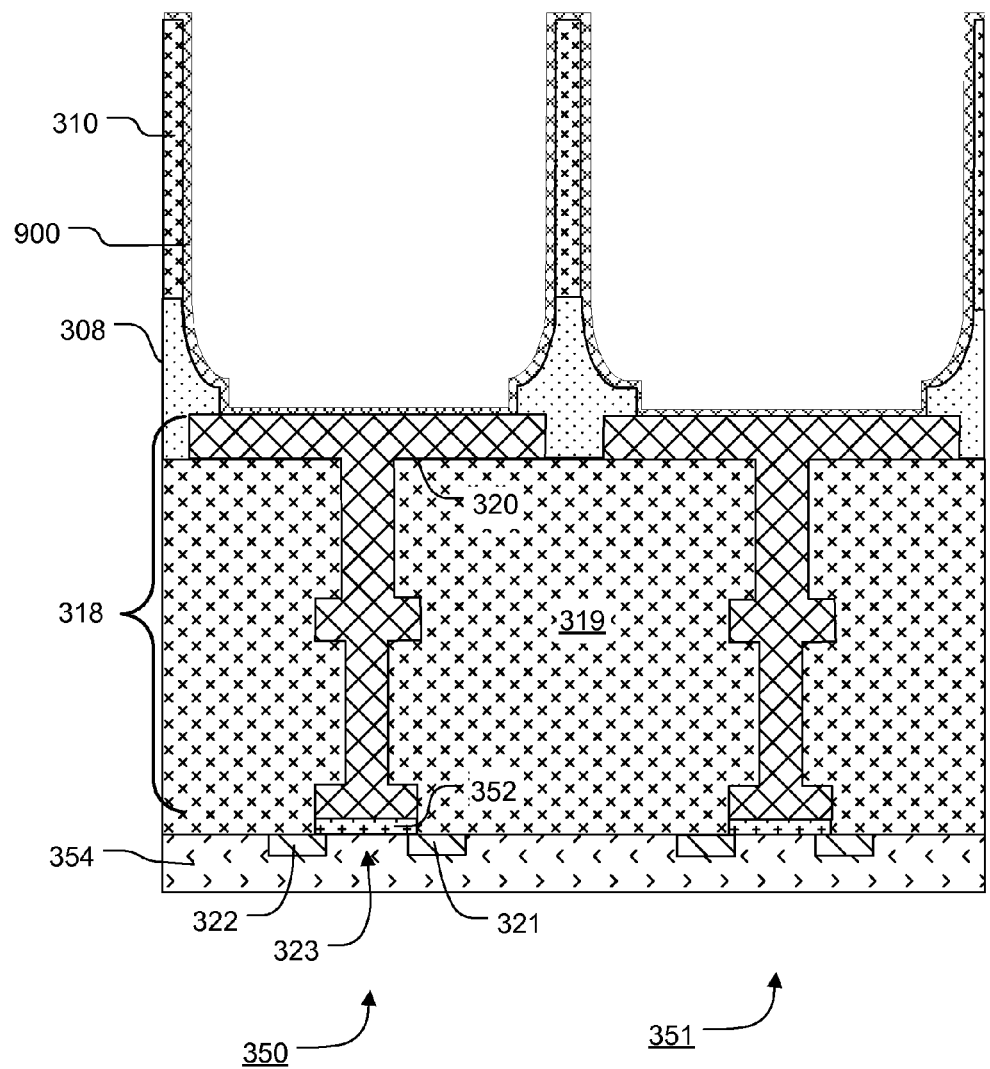
Figure 10:
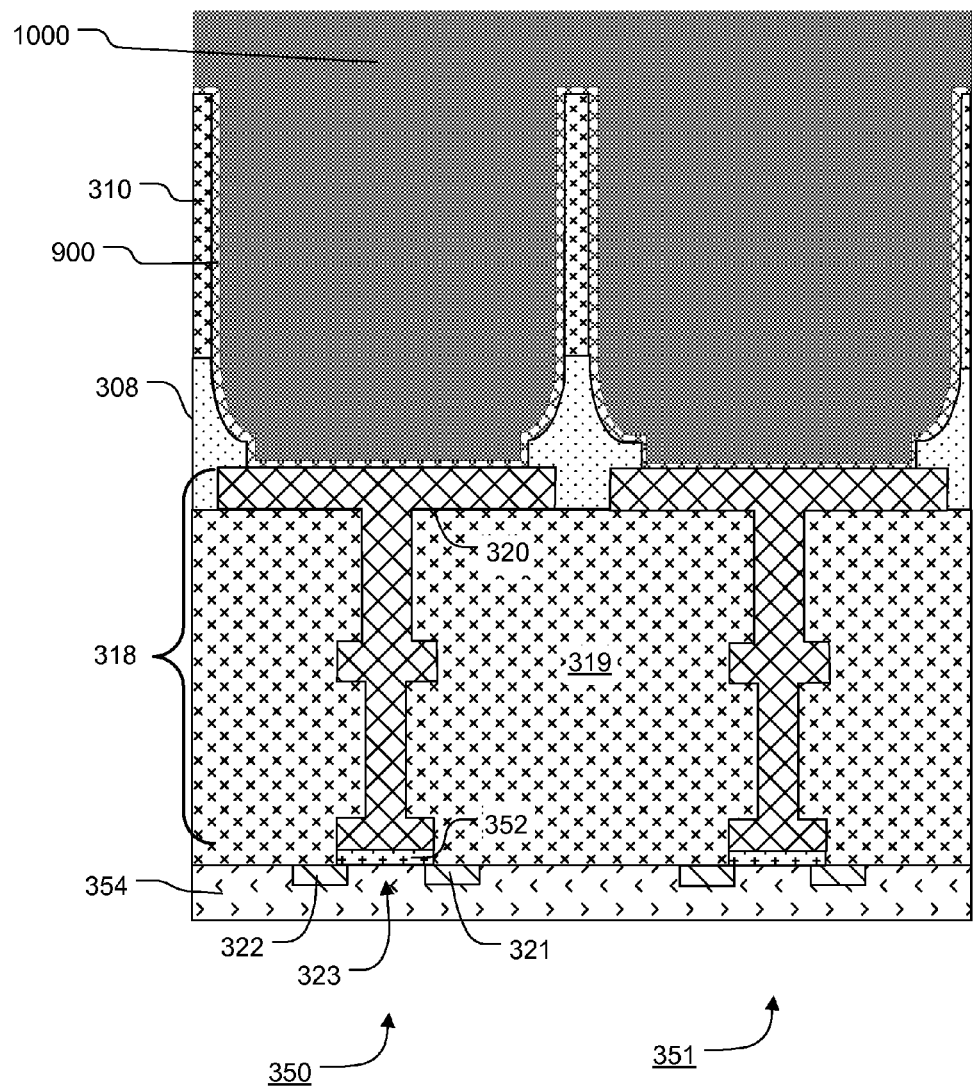
Figure 11:
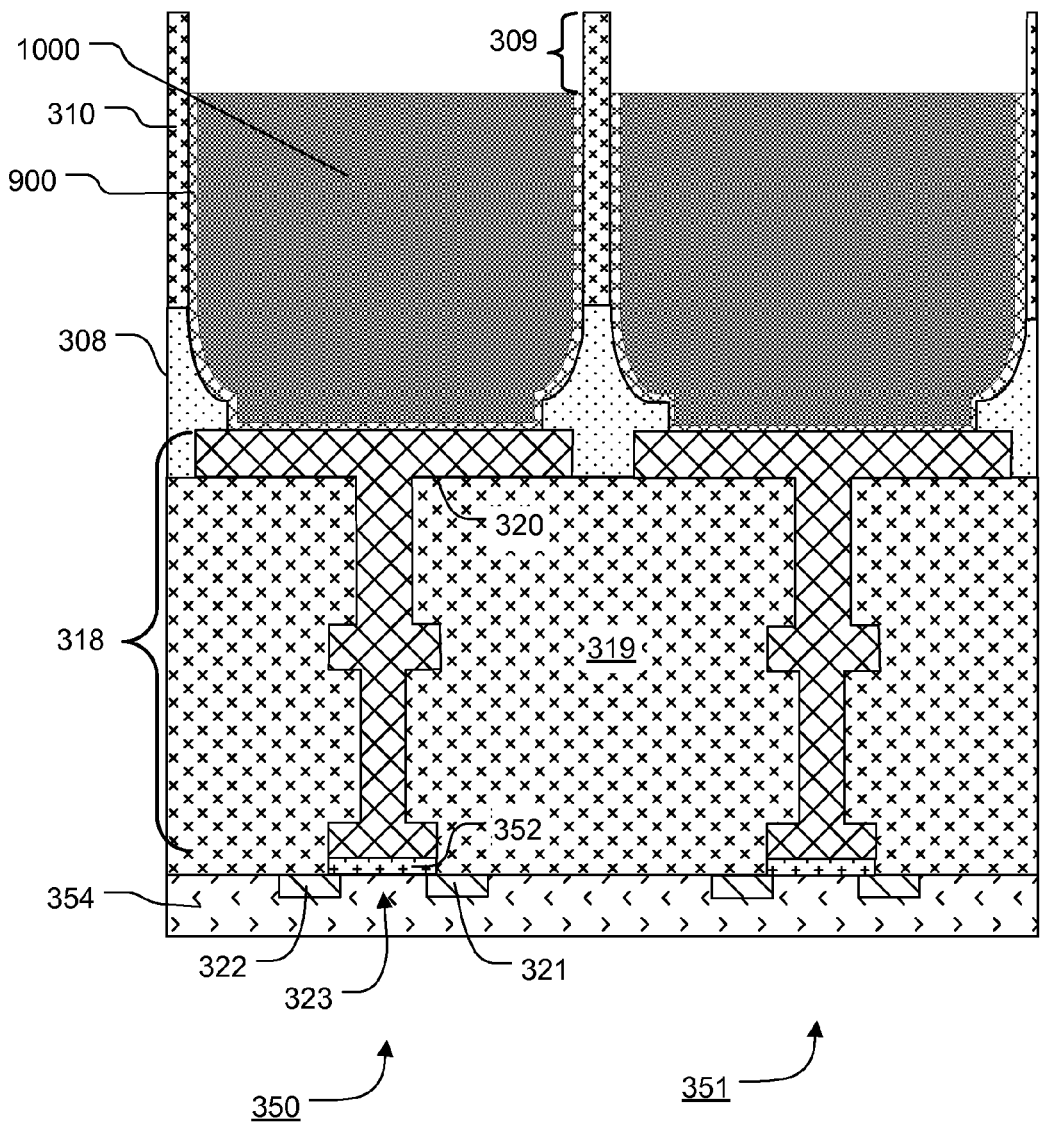
Figure 12:
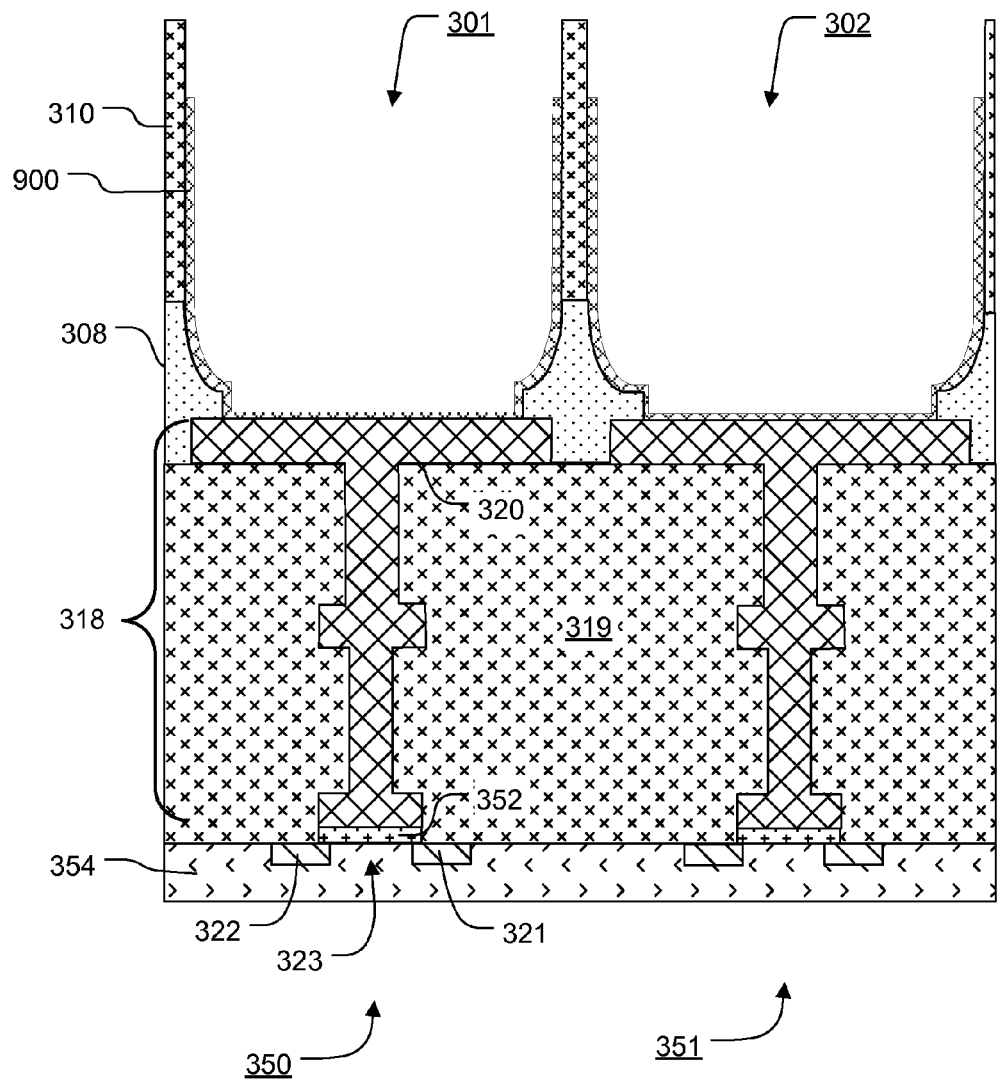

Next, material 1000 is formed on the structure illustrated in FIG. 9, resulting in the structure illustrated in FIG. 10. The material 1000 may comprise one or more layers of deposited dielectric material, such as silicon dioxide or silicon nitride. Alternatively, material 1000 may comprise photoresist. In one embodiment, where the material 1000 comprises photoresist, a partial etch of material 1000 and conductive material 900 is performed such that distance 309 of dielectric material 310 is revealed (that is, distance 309 of sidewall 303 is exposed), resulting in the structure illustrated in FIG. 11. Material 1000 and electrically conductive material 900 may be etched together or separately depending on the process and/or material(s) used. For example, a partial etch may be performed using at least one of an O2 resist etch, Ar sputter breakthrough etch, and Hydrogen Bromide Titanium etch. Next, material 1000 is etched to form openings defining reaction regions 301, 302 extending to the conductive element 370, 900, resulting in the structure illustrated in FIG. 12. In one embodiment, residual photoresist may need to be cleaned from the opening using techniques known to those skilled in the art, for example, O2 plasma ash.

Figure 13:
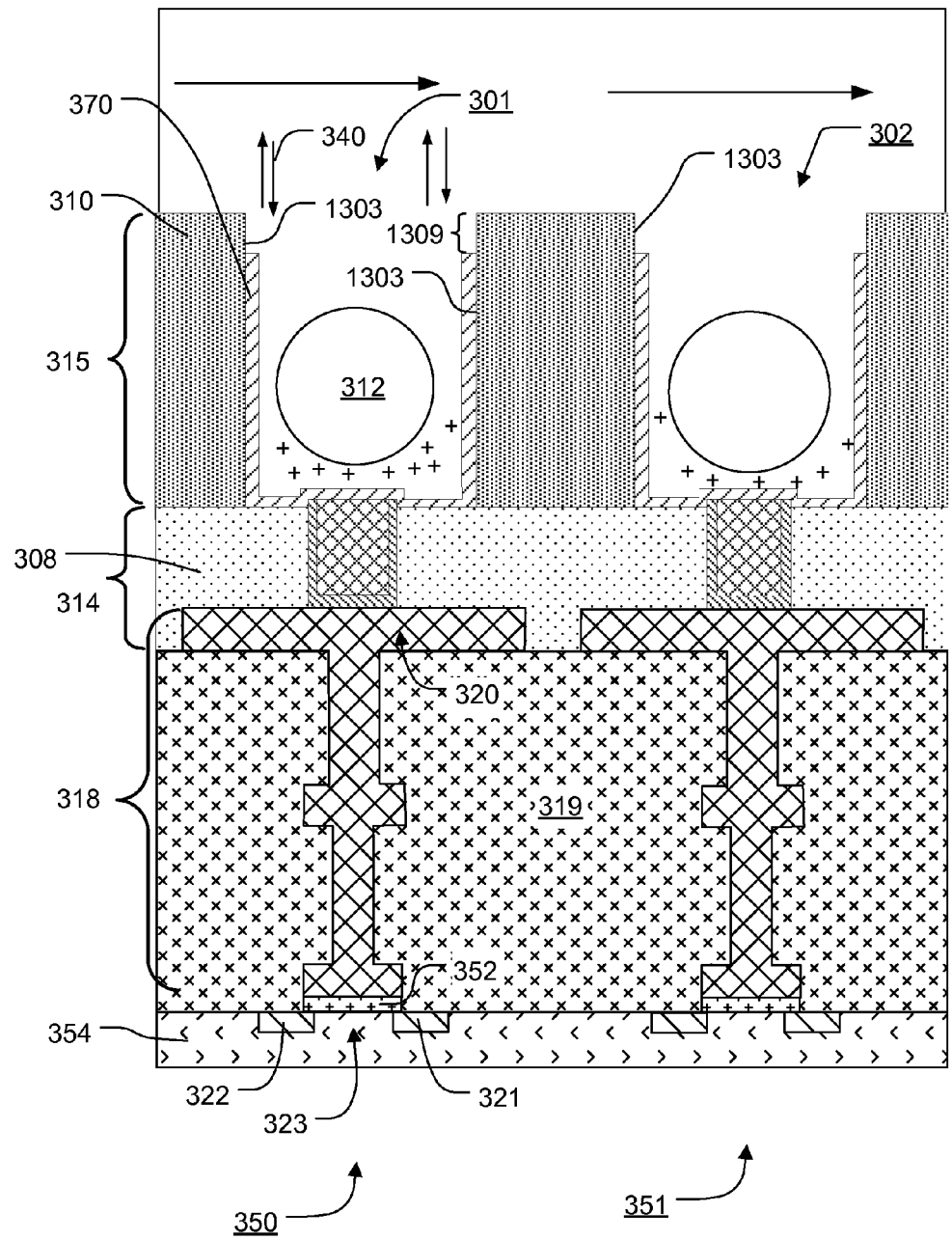
FIGS. 13 to 25 illustrate stages in a manufacturing process for forming an array of chemical sensors and corresponding reaction regions according to a second embodiment.

FIG. 13 illustrates a cross-sectional view of two representative chemical sensors and their corresponding reaction regions according to a second embodiment. The structure of the two representative chemical sensors illustrated in FIG. 13 differs in one aspect from the two representative chemical sensors illustrated in FIG. 3 in that FIG. 13 includes vias over sensor plates 320 on top of which the microwells/nanowells are built. Accordingly, fabrication for the structure in FIG. 3 is different from fabrication of FIG. 13, as is explained in greater detail below.

Figure 14:
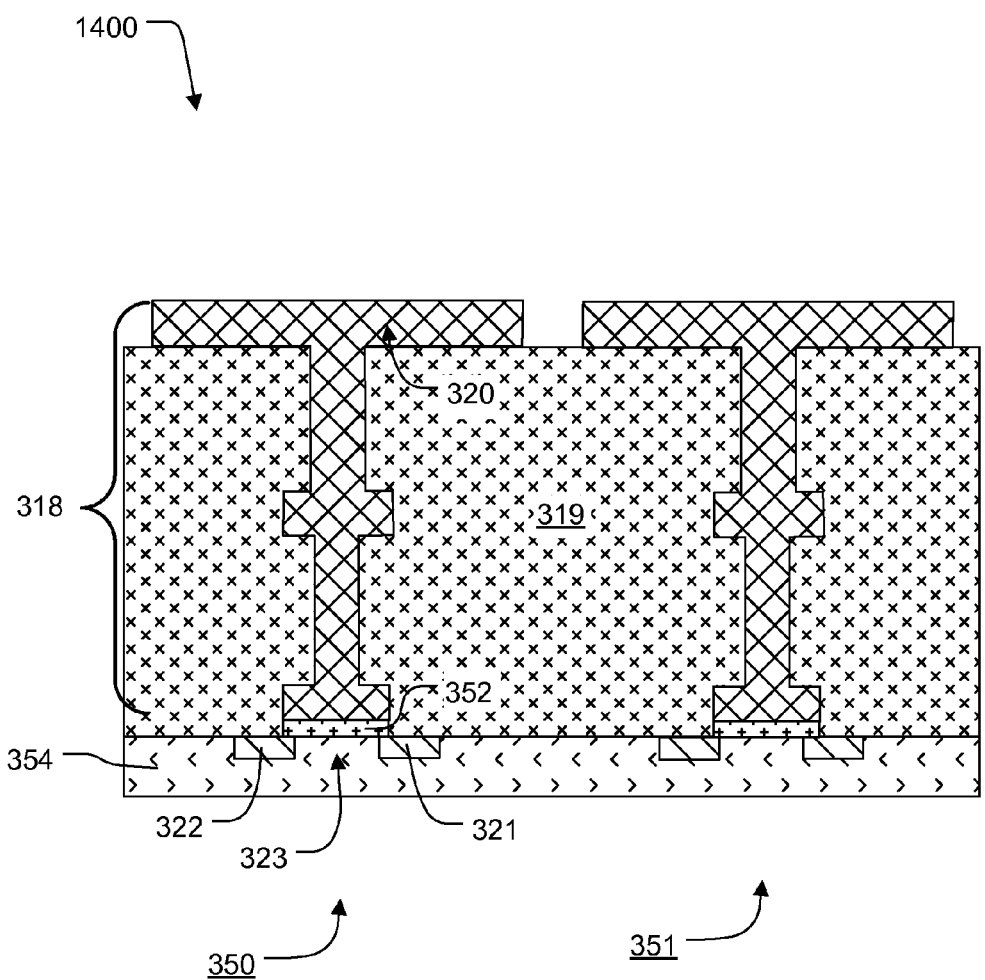
Figure 15:
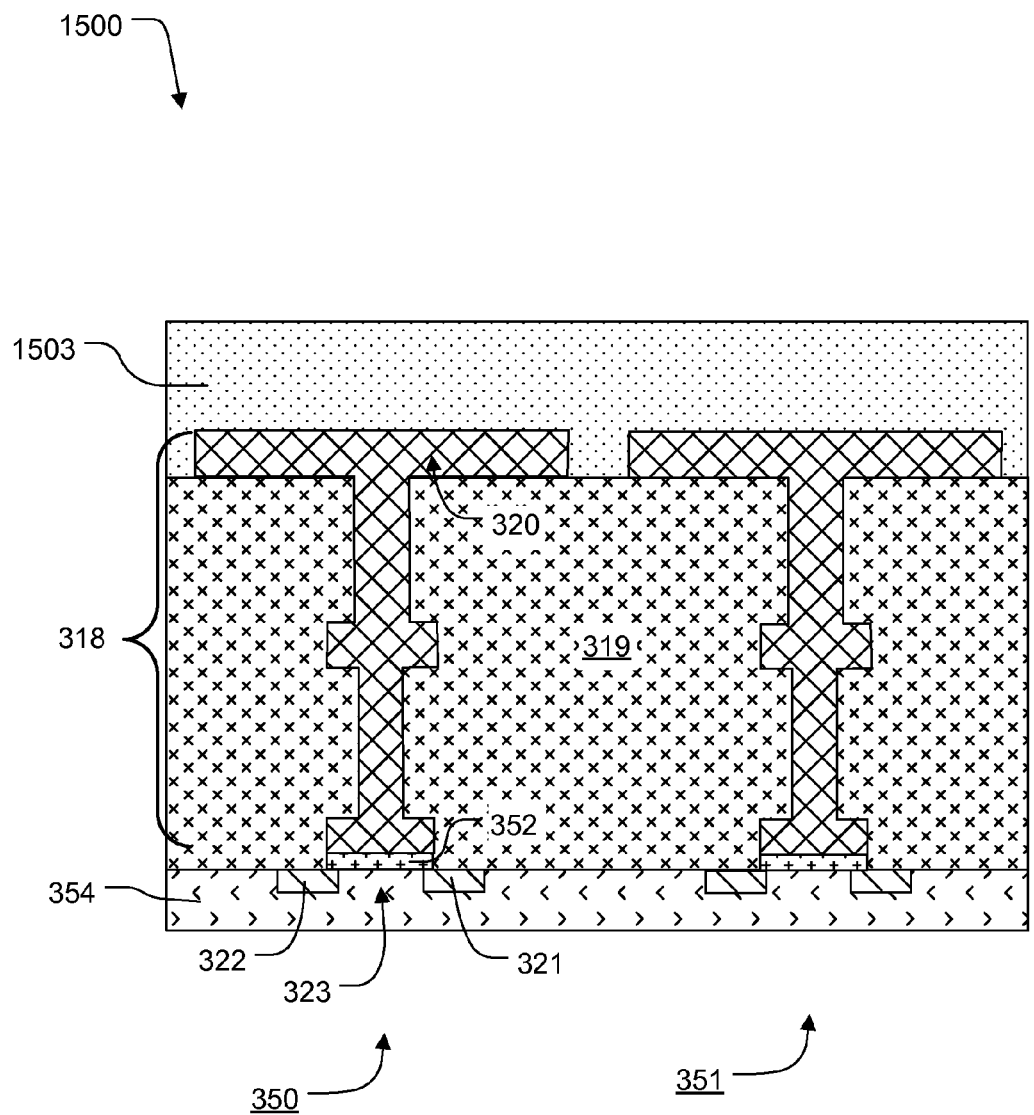
Figure 16:
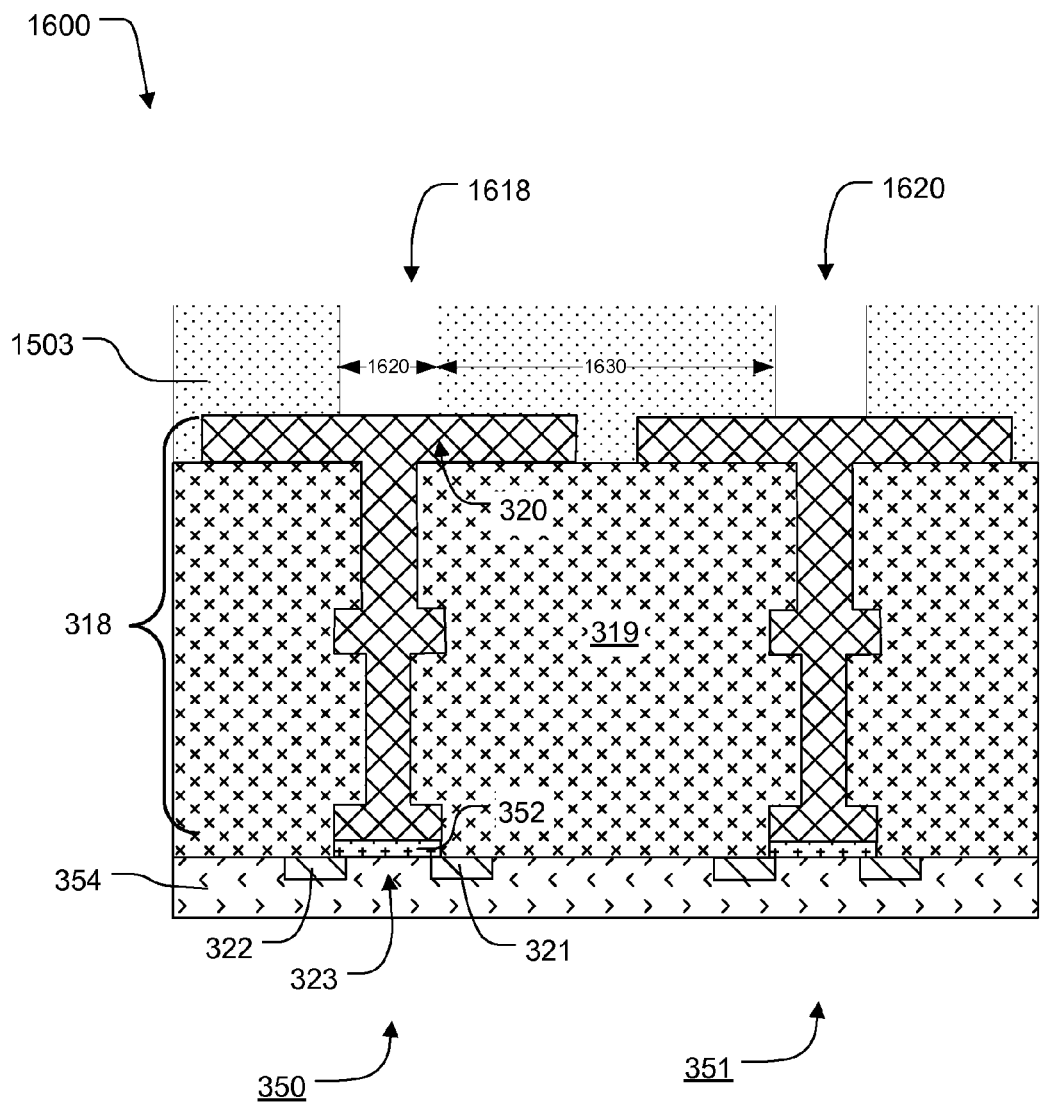

FIGS. 14-25 illustrate stages in a manufacturing process for forming an array of chemical devices and corresponding well structures according to an exemplary embodiment. FIG. 14 illustrates a structure 1400 including the floating gate structures (e.g. floating gate structure 318) for the chemical devices 350, 351. The structure 1400 can be formed in accordance with the structure 400 described in detail above with reference to FIG. 4. As illustrated in the structure 1500 illustrated in FIG. 15, a dielectric material 1503 may be formed on the sensor plate 320 of the field effect transistor of the chemical device 350. Next, as illustrated in FIG. 16, the dielectric material 1503 of the structure 1500 in FIG. 15 is etched to form openings 1618, 1620 (for vias) extending to the upper surfaces of the floating gate structures of the chemical devices 350, 351, resulting in the structure 1600 illustrated in FIG. 16. The openings 1618, 1620 may, for example, be formed by using a lithographic process to pattern a layer of photoresist on the dielectric material 1503 to define the locations of the openings 1618, 1620, and then anisotropically etching the dielectric material 1503 using the patterned photoresist as an etch mask. The anisotropic etching of the dielectric material 1503 may, for example, be a dry etch process, such as a fluorine based Reactive Ion Etching (RIE) process. In the illustrated embodiment, the openings 1618, 1620 are separated by a distance 1630 and the openings 1618, 1620 are of a suitable dimension for a via. For example, the separation distance 1630 may be a minimum feature size for the process (e.g. a lithographic process) used to form the openings 1618, 1620. In such a case, the distance 1630 may be significantly more than the width 1620. Next, a layer of conductive material 1704 is deposited on the structure 1600 illustrated in FIG. 16, resulting in the structure 1700 illustrated in FIG. 17. Conductive material 1704 may be referred to as a conductive liner. The conductive material 1704 may comprise one or more layers of electrically conductive material. For example, the conductive material 1704 may be a layer of titanium nitride, or a layer of titanium. Alternatively, other and/or additional conductive materials may be used, such as those described above with reference to the electrically conductive element. In addition, more than one layer of conductive material may be deposited. The conductive material 1704 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc.

Figure 17:
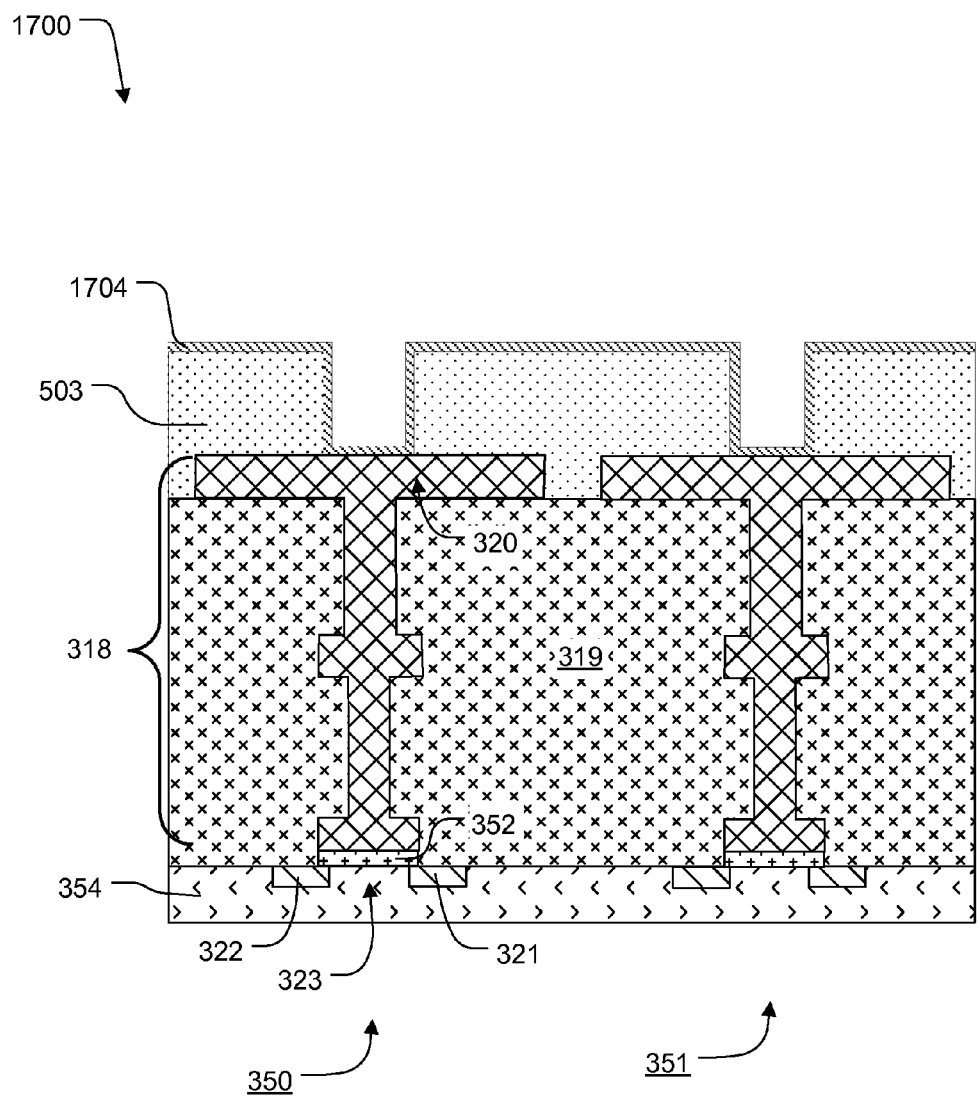
Figure 18:
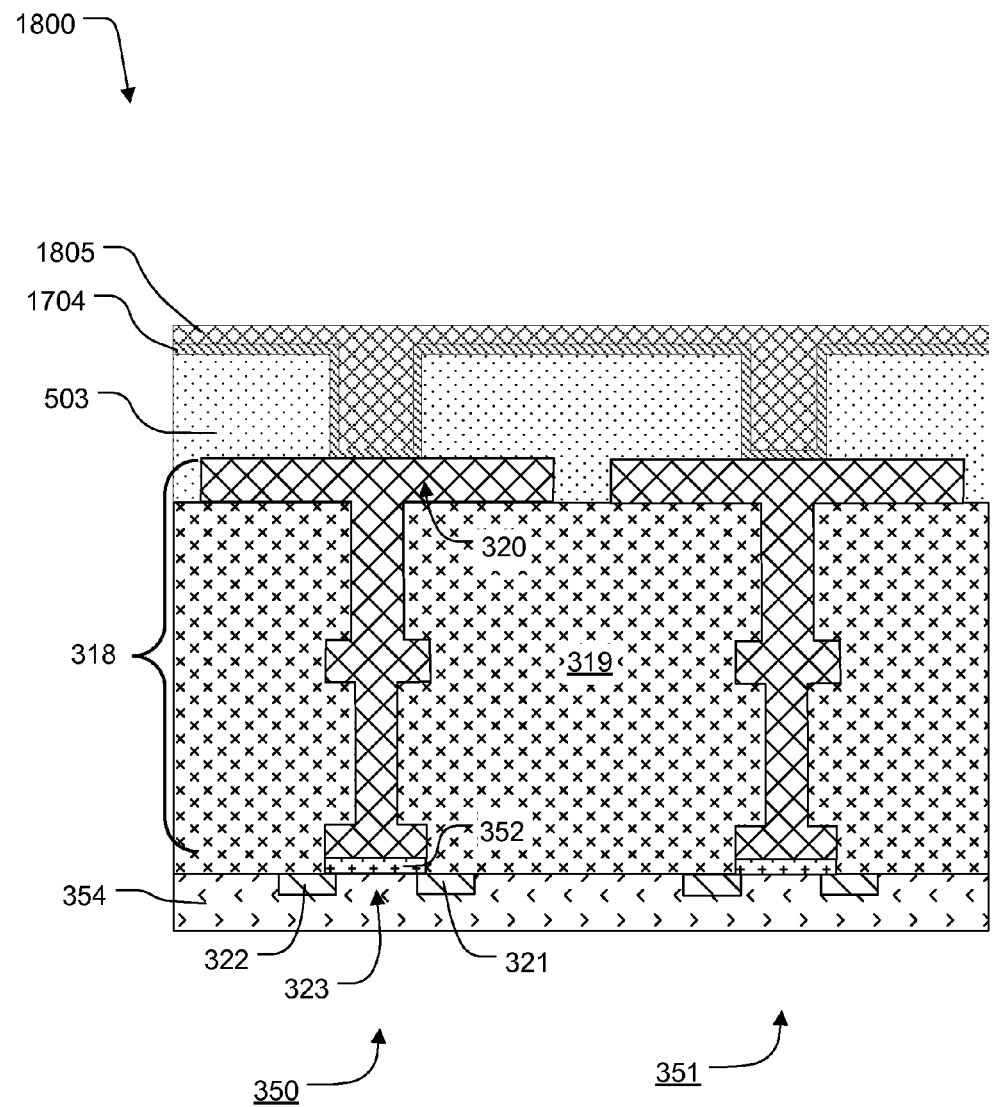

Next, a layer of conductive material 1805 such as tungsten, for example, is deposited on the structure 1700 illustrated in FIG. 17, resulting in the structure 1800 illustrated in FIG. 18. The conductive material 1805 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc. or any other suitable techniques. Next, conductive material 1704 and conductive material 1805 are planarized using a Chemical Mechanical Planarization (CMP) process, for example, resulting in the structure 1900 illustrated in FIG. 19. As an optional, additional step, a via barrier liner (not shown) may be formed on the planarized conductive material 1704 and conductive material 1805. For example, the via barrier liner may comprise titanium nitride.

Figure 19:
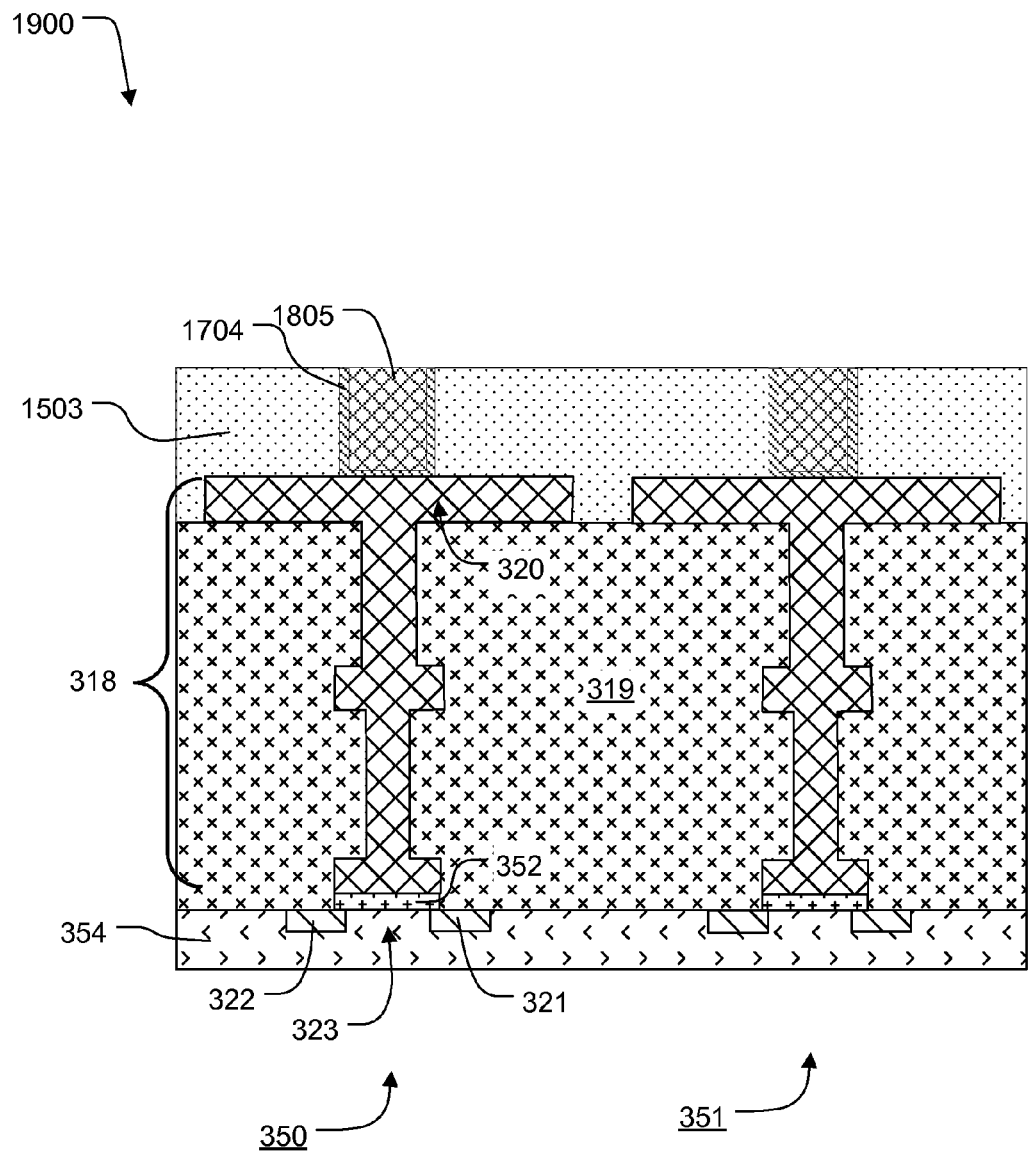
Figure 20:
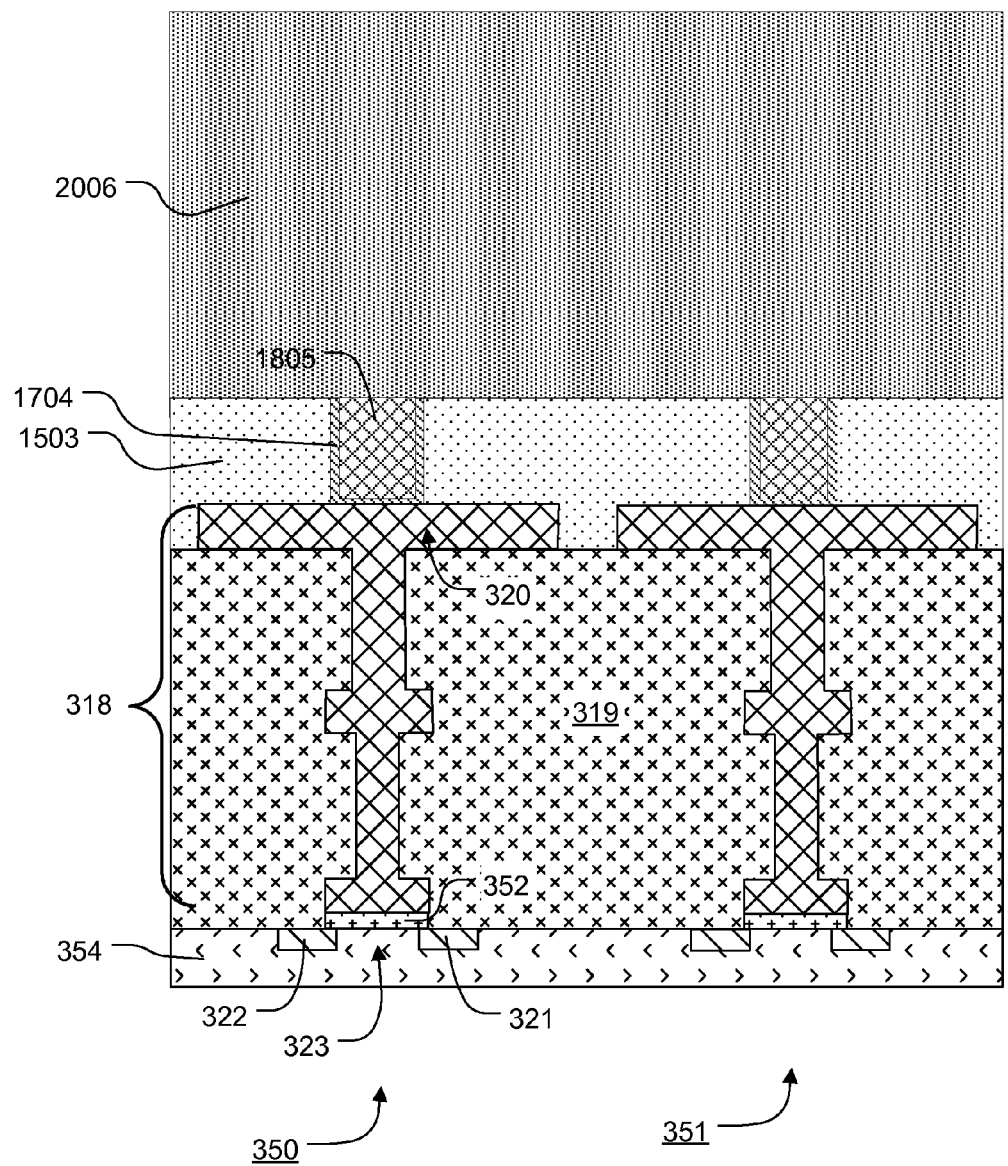
Figure 21:
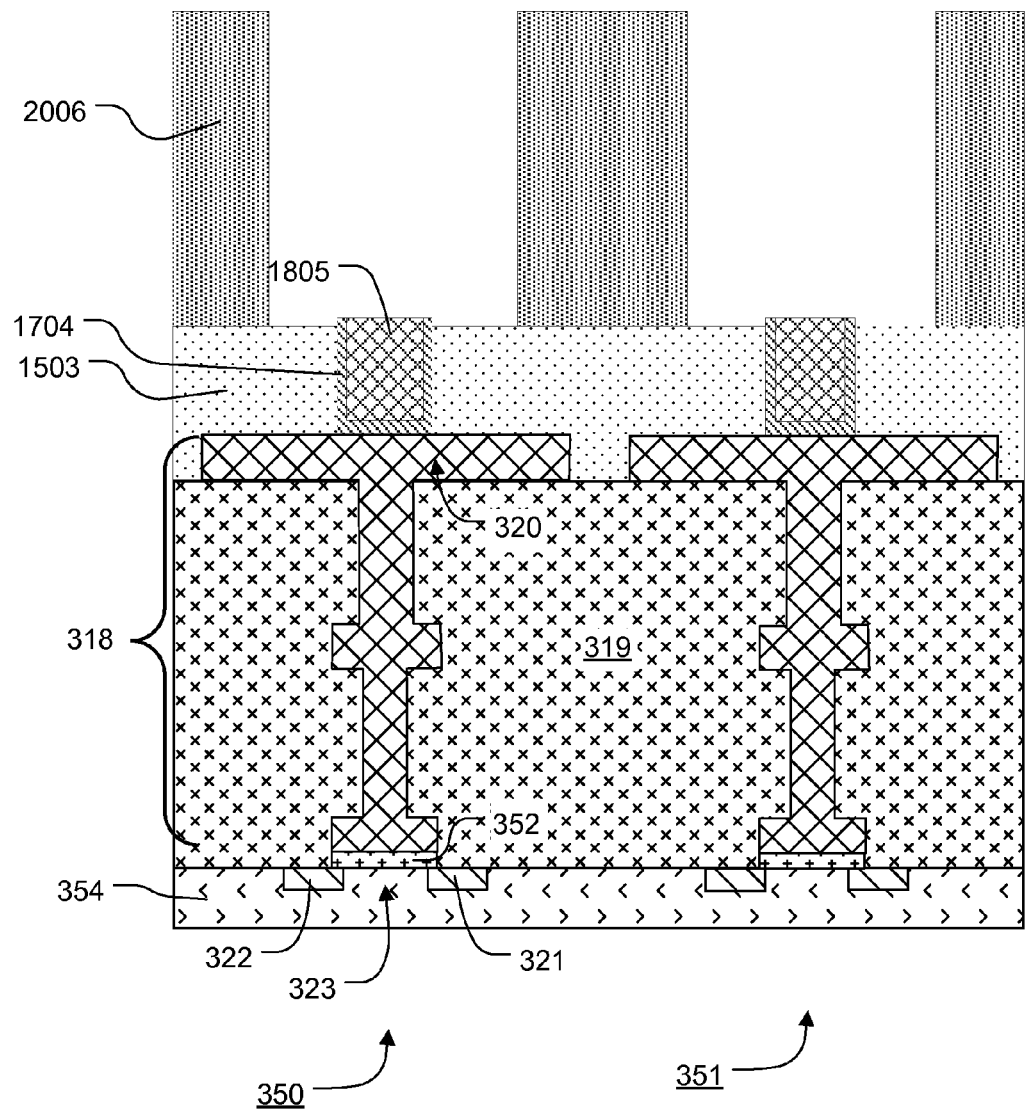

Next, dielectric material 2006 is formed on the structure illustrated in FIG. 19, resulting in the structure illustrated in FIG. 20. The dielectric material 2006 may comprise one or more layers of deposited dielectric material, such as silicon dioxide or silicon nitride. Next, dielectric material 2006 is etched to form openings extending to planarized conductive material 1704 and conductive material 1805 and dielectric material 1503, resulting in the structure illustrated in FIG. 21. Dielectric material 1503 may be partially etched when the openings are formed such that conductive material 1704 and conductive material 1805 are raised above dielectric material 1503 and protrude into the opening, as seen in the illustrated embodiment. Next, a conformal layer of conductive material 2200 is deposited on the structure illustrated in FIG. 21, resulting in the structure illustrated in FIG. 22. The conductive material 2200 comprises one or more layers of electrically conductive material. For example, the conductive material 2200 may be a layer of titanium nitride, or a layer of titanium. Alternatively, other and/or additional conductive materials may be used, such as those described above with reference to the conductive element 370. In addition, more than one layer of conductive material may be deposited. The conductive material 2200 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc.

Figure 22:
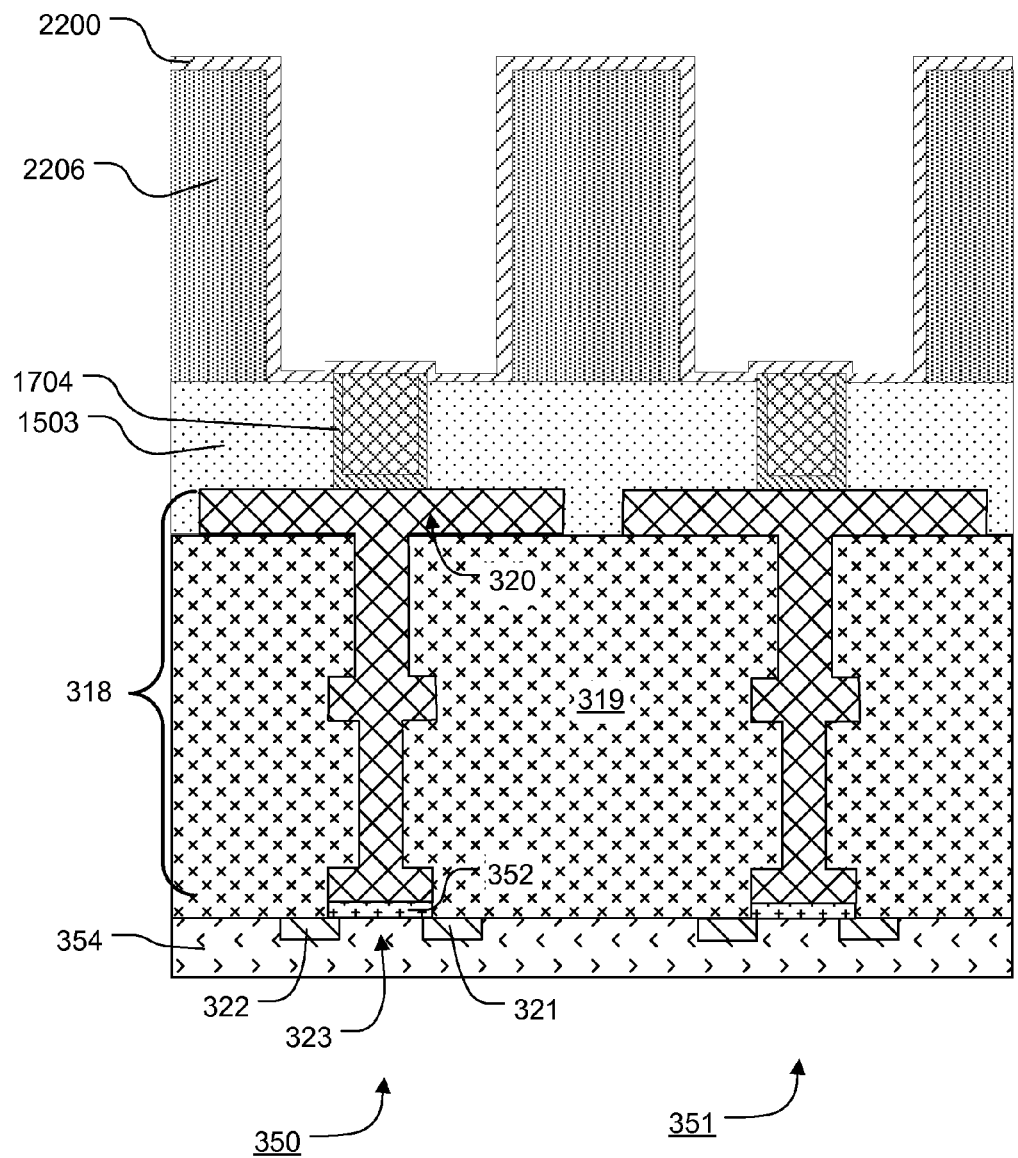
Figure 23:
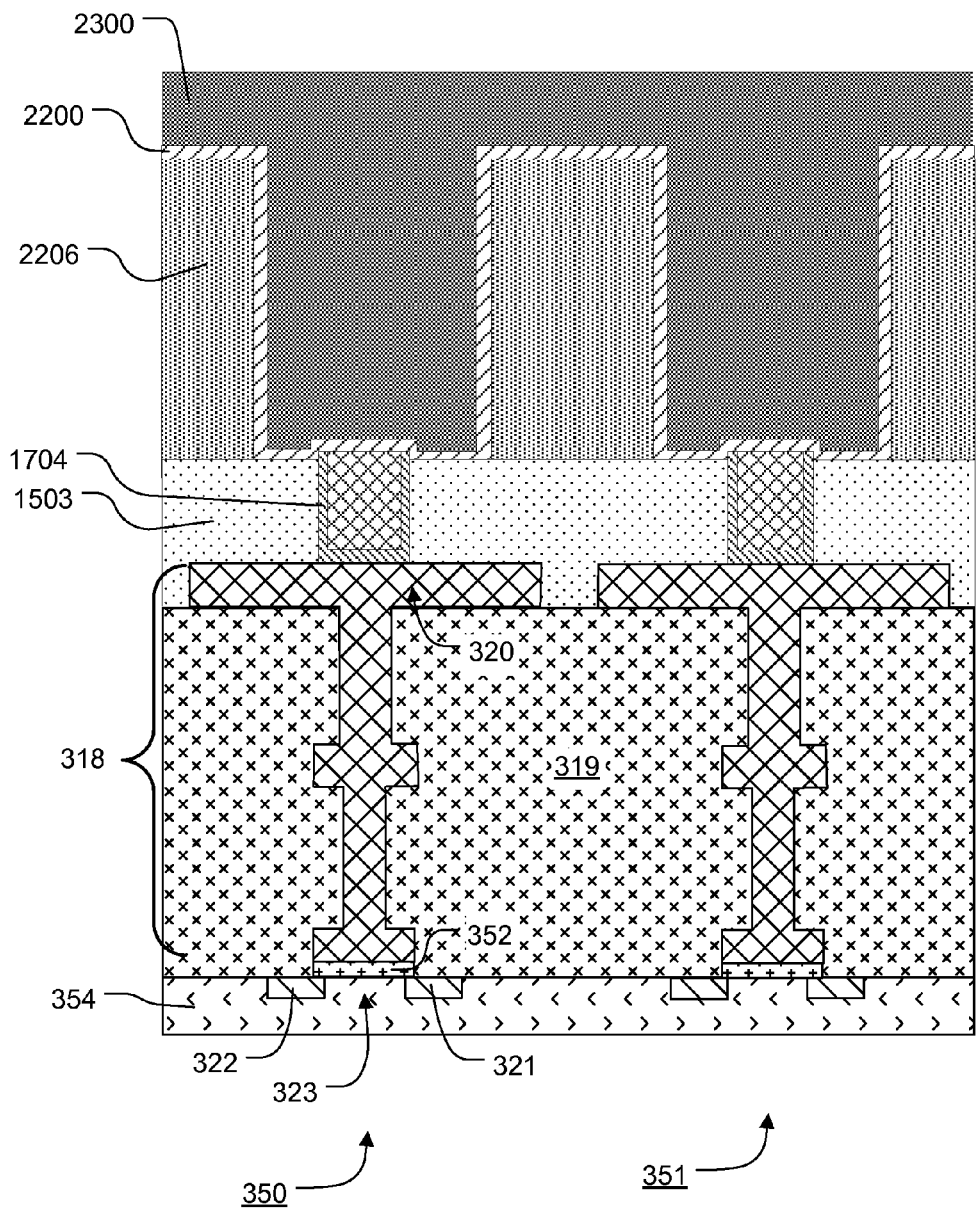
Figure 24:
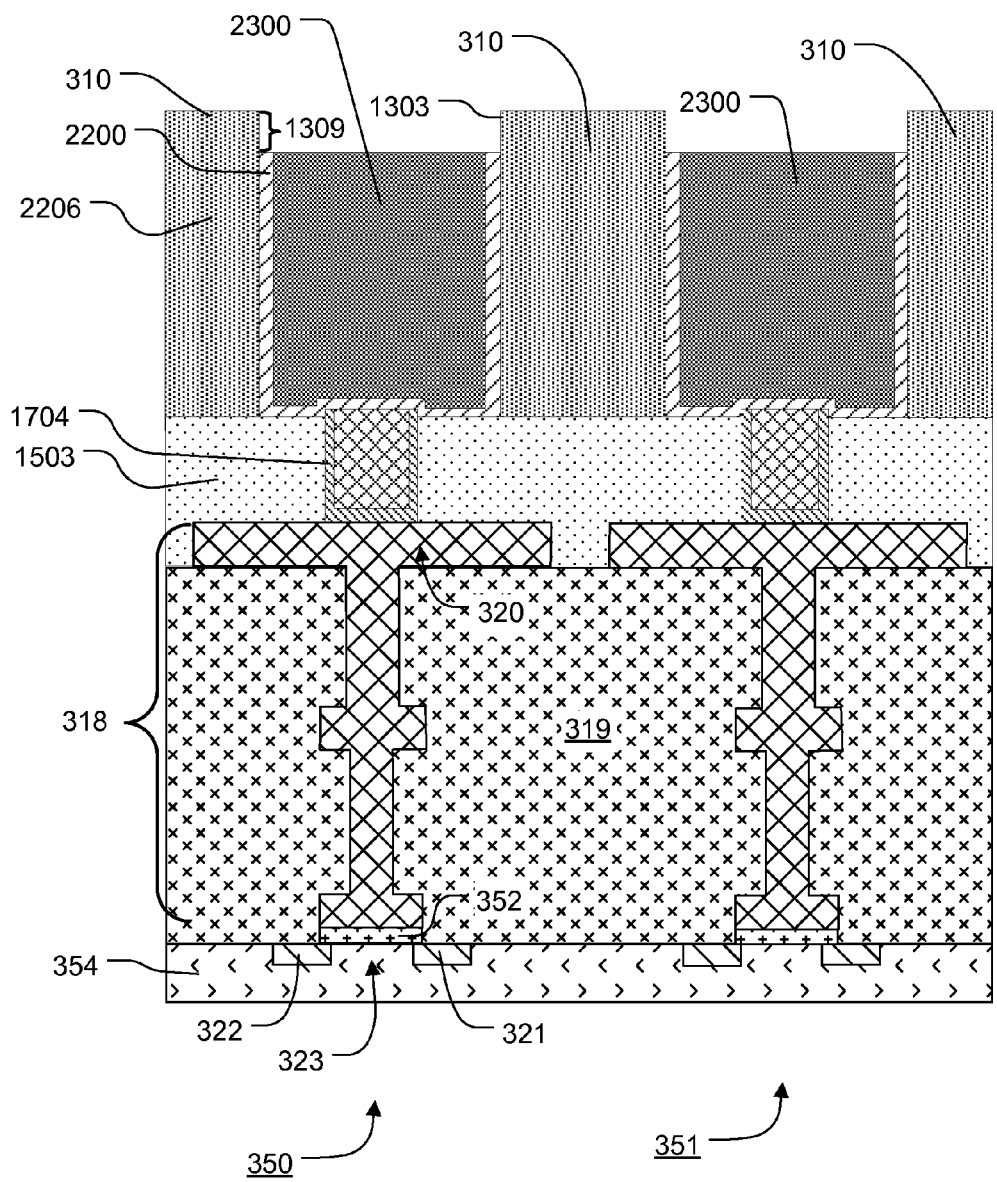
Figure 25:
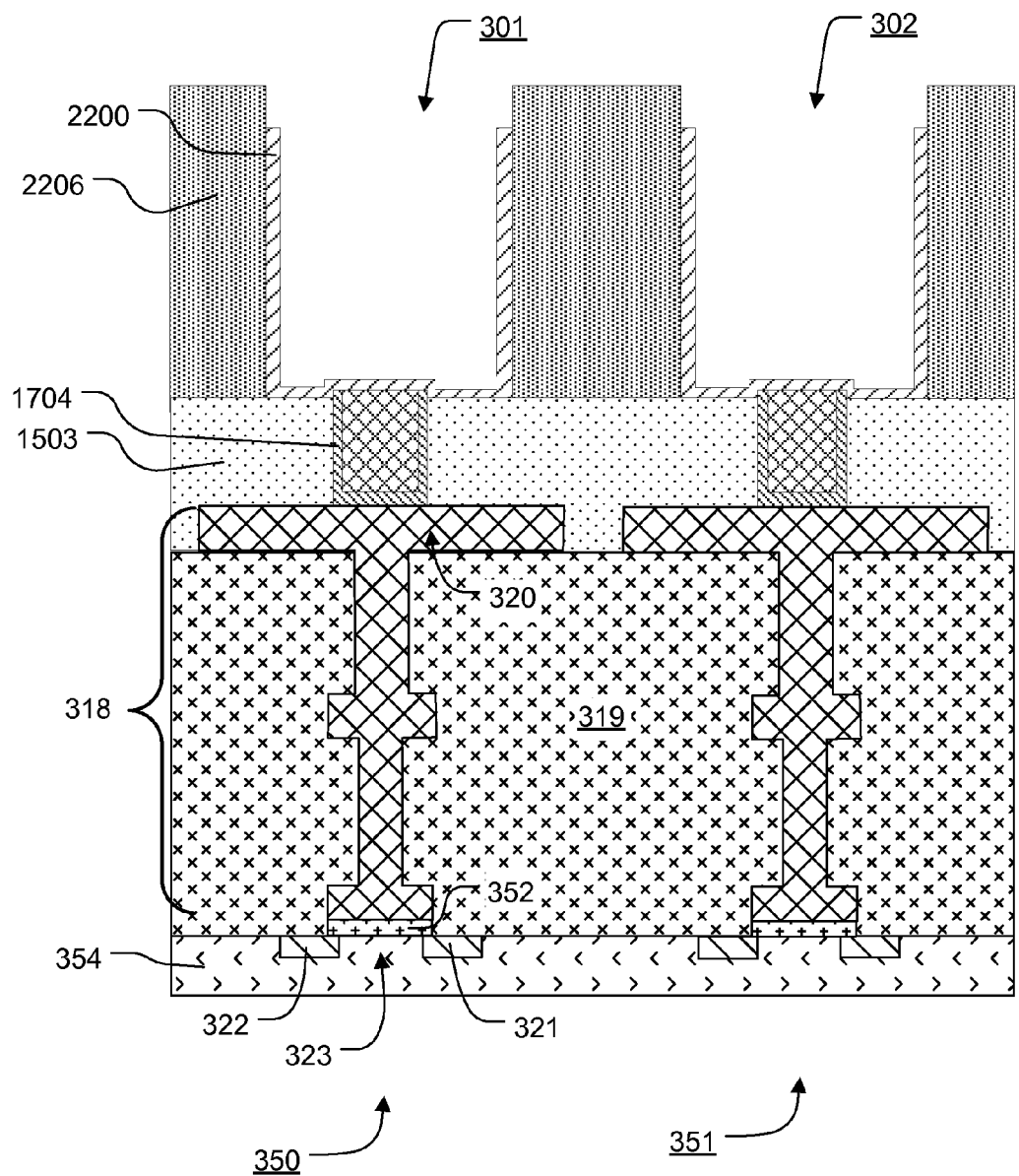

Next, material 2300 is formed on the structure illustrated in FIG. 22, resulting in the structure illustrated in FIG. 23. The material 2300 may comprise one or more layers of deposited dielectric material, such as silicon dioxide or silicon nitride. Alternatively, material 2300 may comprise photoresist. In one embodiment, where the material 2300 comprises photoresist, a partial etch of material 2300 and conductive material 2200 is performed such that distance 1309 of dielectric material 310 is revealed (that is, distance 309 of sidewall 1303 is exposed), resulting in the structure illustrated in FIG. 24. Material 2300 and conductive material 2200 may be etched together or separately depending on the process and/or material(s) used. For example, a partial etch may be performed using at least one of an O2 resist etch, Ar sputter breakthrough etch, and Hydrogen Bromide Titanium etch. Next, material 2300 is etched to form openings defining reaction regions 301, 302 extending to the conductive elements 370, 2200, resulting in the structure illustrated in FIG. 25. In one embodiment, residual photoresist may need to be cleaned from the opening using techniques known to those skilled in the art, for example, O2 plasma ash.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for manufacturing a chemical sensor, the method comprising:
    forming a chemically-sensitive field effect transistor including a floating gate conductor having an upper surface;
    forming a material defining an opening extending to the upper surface of the floating gate conductor, the material comprising a first dielectric underlying a second dielectric; and
    forming a conductive element contacting the upper surface of the floating gate conductor and extending a distance along a sidewall of the opening, wherein forming the material and forming the conductive element include:
    forming the first dielectric on the floating gate conductor, the first dielectric defining a cavity extending to the upper surface of the floating gate conductor;
    depositing the second dielectric thereon;
    etching the second dielectric to expose the upper surface of the floating gate conductor, thereby defining the opening; and
    forming the conductive element within the opening.

2. The method of claim 1, wherein forming the conductive element within the opening comprises:
    depositing a conductive material within the opening and on an upper surface of the first dielectric; and
    removing at least a portion of the conductive material from the upper surface of the second dielectric.

3. The method of claim 2, wherein removing at least the portion of the conductive material comprises:
    depositing a layer of photoresist within the opening and;

removing at least a portion of the conductive material together with the photoresist from the upper surface of the second dielectric.

4. The method of claim 3, further comprising removing remaining photoresist.

5. The method of claim 1, wherein the conductive material comprises titanium.

6. The method of claim 1, wherein the opening is a nanowell.

7. The method of claim 1, wherein the forming a conductive element includes depositing a conductive material conformally within the opening.

8. The method of claim 1, wherein the conductive element includes an inner surface defining a lower portion of a reaction region for the chemical sensor, and the second dielectric includes an inner surface defining an upper portion of the opening.

\* \* \* \* \*